(12) United States Patent
Silverstein et al.

(10) Patent No.: US 11,548,986 B2
(45) Date of Patent: Jan. 10, 2023

(54) HIPE-TEMPLATED ZWITTERIONIC HYDROGELS, PROCESS OF PREPARATION AND USES THEREOF

(71) Applicant: Technion Research & Development Foundation Limited, Haifa (IL)

(72) Inventors: Michael S. Silverstein, Zikhron-Yaakov (IL); Tao Zhang, Nesher (IL)

(73) Assignee: Technion Research & Development Foundation Limited, Haifa (IL)

( * ) Notice: Subject to any disclaimer, the term of this patent is extended or adjusted under 35 U.S.C. 154(b) by 211 days.

(21) Appl. No.: 16/758,882

(22) PCT Filed: Oct. 30, 2018

(86) PCT No.: PCT/IL2018/051158
§ 371 (c)(1),
(2) Date: Apr. 24, 2020

(87) PCT Pub. No.: WO2019/087185
PCT Pub. Date: May 9, 2019

(65) Prior Publication Data
US 2020/0277450 A1    Sep. 3, 2020

(30) Foreign Application Priority Data

Nov. 2, 2017 (IL) .......................... 255404

(51) Int. Cl.
C08J 3/075 (2006.01)
A61L 15/24 (2006.01)
A61L 15/60 (2006.01)

(52) U.S. Cl.
CPC .............. *C08J 3/075* (2013.01); *A61L 15/24* (2013.01); *A61L 15/60* (2013.01); *C08J 2300/10* (2013.01)

(58) Field of Classification Search
CPC ....... C08J 3/075; C08J 2300/10; A61L 15/24; A61L 15/60
See application file for complete search history.

(56) References Cited

U.S. PATENT DOCUMENTS

| | | |
|---|---|---|
| 2,801,185 A | 7/1957 | Iler |
| 3,417,171 A | 12/1968 | Eberle et al. |
| 4,455,205 A | 6/1984 | Olson et al. |
| 4,478,876 A | 10/1984 | Chung |
| 4,486,504 A | 12/1984 | Chung |
| 4,491,508 A | 1/1985 | Olson et al. |
| 4,522,958 A | 6/1985 | Das et al. |
| 5,258,225 A | 11/1993 | Katsamberis |
| 5,648,407 A | 7/1997 | Goetz et al. |
| 5,652,194 A | 7/1997 | Dyer et al. |
| 6,147,131 A | 11/2000 | Mork et al. |
| 6,204,298 B1 | 3/2001 | DesMarais et al. |
| 6,241,713 B1 | 6/2001 | Gross et al. |
| 6,353,037 B1 | 3/2002 | Thunhorst et al. |
| 6,573,305 B1 | 6/2003 | Thunhorst et al. |
| 6,586,483 B2 | 7/2003 | Kolb et al. |
| 6,750,261 B1 | 6/2004 | Clear et al. |
| 7,129,277 B2 | 10/2006 | Baran, Jr. |
| 7,189,768 B2 | 3/2007 | Baran, Jr. et al. |
| 7,507,780 B2 | 3/2009 | Hagerty et al. |
| 7,967,367 B2 | 6/2011 | Cafeo et al. |
| 10,449,516 B2 | 10/2019 | Kovacic et al. |
| 10,851,218 B2 | 12/2020 | Silverstein et al. |
| 2002/0091368 A1 | 7/2002 | LaVon et al. |
| 2003/0097103 A1 | 5/2003 | Horney et al. |
| 2003/0170308 A1 | 9/2003 | Cleary et al. |
| 2004/0116594 A1 | 6/2004 | Bhattacharjee et al. |
| 2004/0204510 A1* | 10/2004 | Clear ..................... C08J 7/0427 521/65 |
| 2004/0224021 A1 | 11/2004 | Omidian et al. |
| 2005/0215962 A1 | 9/2005 | Litvay et al. |
| 2006/0010004 A1 | 1/2006 | Deckner |
| 2009/0215913 A1 | 8/2009 | Thies et al. |
| 2009/0270538 A1 | 10/2009 | Ikeuchi et al. |
| 2011/0091512 A1* | 4/2011 | Li ............................. C08J 9/16 521/146 |
| 2012/0201806 A1 | 8/2012 | Silverstein et al. |
| 2012/0261803 A1 | 10/2012 | Wang et al. |
| 2013/0216814 A1 | 8/2013 | Hirao et al. |
| 2013/0324627 A1 | 12/2013 | Silverstein et al. |
| 2014/0011897 A1 | 1/2014 | Friederichs et al. |
| 2014/0328884 A1 | 11/2014 | Reyes et al. |
| 2015/0166753 A1 | 6/2015 | Silverstein et al. |
| 2016/0287516 A1 | 10/2016 | Cosgriff-Hernandez et al. |
| 2016/0361382 A1 | 12/2016 | Steinbach-Rankins et al. |

(Continued)

FOREIGN PATENT DOCUMENTS

| CA | 2322498 | 9/1999 |
|---|---|---|
| CN | 107126936 | 9/2017 |

(Continued)

OTHER PUBLICATIONS

Annabi, N. et al. "Controlling the Porosity and Microarchitecture of Hydrogels for Tissue Engineering" Tissue Engineering: Part B 2010, 16 (4), 371-383 (Year: 2010).*
International Preliminary Report on Patentability dated Jan. 10, 2019 From the International Bureau of WIPO Re. Application No. PCT/IL2017/050706. (10 Pages).
International Preliminary Report on Patentability dated May 14, 2020 From the International Bureau of WIPO Re. Application No. PCT/IL2018/051158. (6 Pages).
International Preliminary Report on Patentability dated Jan. 23, 20120 From the International Bureau of WIPO Re. Application No. PCT/IL2018/050751. (10 Pages).
International Preliminary Report on Patentability dated Feb. 28, 2019 From the International Bureau of WIPO Re. Application No. PCT/IL2017/050904. (8 Pages).

(Continued)

*Primary Examiner* — Andrew S Rosenthal

(57) ABSTRACT

A compositions-of-matter in the form of HIPE-templated hydrogels, comprising a crosslinked polymer of zwitterionic monomers, which exhibit unusual antipolyelectrolyte characteristics, dual pH-, and temperature-responsiveness, as well as processes of obtaining the same and using the same.

17 Claims, 5 Drawing Sheets

(56) References Cited

U.S. PATENT DOCUMENTS

| | | |
|---|---|---|
| 2017/0189238 A1 | 7/2017 | Andrews |
| 2017/0326529 A1 | 11/2017 | Kovacic et al. |
| 2019/0031845 A1 | 1/2019 | Kitayama et al. |
| 2019/0127546 A1 | 5/2019 | Silverstein et al. |
| 2019/0194083 A1 | 6/2019 | Silverstein et al. |
| 2020/0016574 A1 | 1/2020 | Kovacic et al. |
| 2020/0123338 A1 | 4/2020 | Silverstein et al. |
| 2020/0148837 A1 | 5/2020 | Silverstein et al. |

FOREIGN PATENT DOCUMENTS

| | | |
|---|---|---|
| WO | WO 94/12134 | 6/1994 |
| WO | WO 02/008321 | 1/2002 |
| WO | WO 2009/013500 | 1/2009 |
| WO | WO 2015/076908 | 5/2015 |
| WO | WO 2018/002916 | 1/2018 |
| WO | WO 2018/002916 A8 | 1/2018 |
| WO | WO 2018/033913 | 2/2018 |
| WO | WO 2018/033913 A8 | 2/2018 |
| WO | WO 2019/012529 | 1/2019 |
| WO | WO 2019/016816 | 1/2019 |
| WO | WO 2019/016816 A9 | 5/2019 |
| WO | WO 2019/087185 | 5/2019 |

OTHER PUBLICATIONS

International Preliminary Report on Patentability dated Jan. 30, 2020 From the International Bureau of WIPO Re. Application No. PCT/IL2018/050803. (7 Pages).
International Search Report and the Written Opinion dated Nov. 1, 2018 From the International Searching Authority Re. Application No. PCT/IL2018/050803. (11 Pages).
International Search Report and the Written Opinion dated Nov. 12, 2017 From the International Searching Authority Re. Application No. PCT/IL2017/050904. (13 Pages).
International Search Report and the Written Opinion dated Nov. 20, 2018 From the International Searching Authority Re. Application No. PCT/IL2018/050751. (15 Pages).
International Search Report and the Written Opinion dated Jan. 27, 2019 From the International Searching Authority Re. Application No. PCT/IL2018/051158. (12 Pages).
International Search Report and the Written Opinion dated Sep. 27, 2017 From the International Searching Authority Re. Application No. PCT/IL2017/050706. (17 Pages).
Notice of Allowance dated Jun. 13, 2019 From the US Patent and Trademark Office Re. U.S. Appl. No. 15/595,970. (23 Pages).
Notice of Allowance dated Jul. 22, 2020 from the US Patent and Trademark Office Re. U.S. Appl. No. 16/231,627. (33 pages).
Notice of Omitted Item(s) in A Nonprovisional Application dated Jan. 8, 2015 From the US Patent and Trademark Office Re. U.S. Appl. No. 14/578,519.
Office Action and Search Report dated Mar. 1, 2017 From the Israel Patent Office Re. Application No. 247302. (7 Pages).
Office Action and Search Report dated Dec. 4, 2016 From the Israel Patent Office Re. Application No. 245656. (7 Pages).
Office Action and Search Report dated Sep. 5, 2018 From the Israel Patent Office Re. Application No. 256783. (14 Pages).
Office Action and Search Report dated Mar. 11, 2018 From the Israel Patent Office Re. Application No. 255404. (7 Pages).
Office Action and Search Report dated Mar. 16, 2017 From the Israel Patent Office Re. Application No. 246468. (8 Pages).
Office Action dated Sep. 7, 2017 From the Israel Patent Office Re. Application No. 247302 and Its Translation Into English. (12 Pages).
Office Action dated Feb. 8, 2018 From the Israeli Patent Office Re. Application No. 247302 and Its Translation Into English. (11 Pages).
Office Action dated Jul. 16, 2017 From the Israel Patent Office Re. Application No. 245656 and Its Translation Into English. (4 Pages).
Office Action dated Dec. 28, 2017 From the Israel Patent Office Re. Application No. 253431. (4 Pages).
Office Action dated Sep. 28, 2017 From the Israel Patent Office Re. Application No. 246468 and Its Translation Into English. (6 Pages).
Office Action dated Aug. 30, 2018 From the Israel Patent Office Re. Application No. 247302 and Its Translation Into English. (13 Pages).
Office Action dated Feb. 8, 2018 From the Israel Patent Office Re. Application No. 246468 and Its Translation Into English. (4 Pages).
Official Action dated Sep. 5, 2014 From the US Patent and Trademark Office Re. U.S. Appl. No. 13/369,362.
Official Action dated Oct. 6, 2015 From the US Patent and Trademark Office Re. U.S. Appl. No. 14/578,519.
Official Action dated May 13, 2014 From the US Patent and Trademark Office Re. U.S. Appl. No. 13/892,606.
Official Action dated Nov. 20, 2018 From the US Patent and Trademark Office Re. U.S. Appl. No. 15/595,970. (38 Pages).
Official Action dated Jun. 29, 2020 from the US Patent and Trademark Office Re. U.S. Appl. No. 16/579,942. (26 pages).
Restriction Official Action dated Apr. 7, 2020 from the US Patent and Trademark Office Re. U.S. Appl. No. 16/231,627. (10 pages).
Supplementary European Search Report and the European Search Opinion dated May 12, 2020 From the European Patent Office Re. Application No. 17841212.8. (7 Pages).
Supplementary European Search Report and the European Search Opinion dated Jan. 22, 2020 From the European Patent Office Re. Application No. 17819486.6. (11 Pages).
Audouin et al. "Preparation, Solid-State NMR, and Physicochemical Characterization of Surprisingly Tough Open Cell PolyHIPEs Derived From 1-Vinyl-1,2,4-Triazole Oil-in-Water Emulsions", Macromolecules, 44(12): 4879-4886, May 27, 2011.
Audouin et al. "Synthesis of Porous Materials by 2-Nitroresorcinol/Cyanuric Chloride Thermal Polycondensation in Emulsions", Journal of Applied Polymer Science, 108(5): 280802813, Published Online Feb. 25, 2008.
Avraham "Liraz Avraham—Materials Engineer—GOI (Government of Israel)", LinkedIn, XP055657899, 6 P., Jan. 14, 2020.
Avraham et al. "Porous, Polysaccharide-Containing Poly(Urethane Urea) Monoliths Through Emulsion Templating", Department of Materials Science and Engineering, Technion—Israel Institute of Technology, XP055657891, 1 P., Dec. 31, 2015.
Barbetta et al. "High Internal Phase Emulsions (HIPEs) Containing Divinylbenzene and 4-Venylbenzyl Chloride and the Morphology of the Resulting PolyHIPE Materials", Chemical Communications, p. 221-222, 2000.
Chung et al. "The Thermoresponsive Shape Memory Characteristics of Polyurethane Foam", Journal of Applied Polymer Science, 117: 2265-2271, 2010.
Cohen Samoocha "Bicontinuous Hydrogel-Filled Hydrophobic Polymers Synthesized Within Polymer-Nanoparticle-Stabilized Pickering Emulsions", M.Sc Thesis, Department of Materials Science and Engineering, Abstract. Apr. 2015.
Colver et al. "Cellular Polymer Monoliths Made Via Pickering High Internal Phase Emulsions", Chemical Materials, 19: 1537-1539, 2007.
David et al. "Porous Polyurethanes Synthesized Within High Internal Phase Emulsions", Journal of Polymer Science Part A: Polymer Chemistry, XP055450683, 47(21): 5806-5814, Sep. 28, 2009. Abstract, Fig.3, p. 5807-5808, p. 5809, Line 2, 5813.
David et al. "Porous Polyurethanes Synthesized within High Internal Phase Emulsions", Journal of Polymer Science: Part A: Polymer Chemistry, 2002(23): 5806-5814, 2009.
Deleuze et al. "Preparation and Functionalisation of Emulsion-Derived Microcellular Polymeric Foams (PolyHIPEs) by Ring-Opening Metathesis Polymerisation (ROMP)", Chemistry Communications, 2002(23): 2822-2823, Advance Publication Oct. 25, 2002.
Gitli et al. "Emulsion Templated Bicontinuous Hydrophobic-Hydrophilic Polymers: Loading and Release", Polymer, 52(1): 107-115, Available Online Nov. 13, 2010.
Gurevitch et al. "Nanoparticle-Based and Organic-Phase-Based AGET ATRP PolyHIPE Synthesis Within Pickering HIPEs and Surfactants-Stabilized HIPEs", Macromolecules, 44(9): 3398-3409, Apr. 15, 2011.

(56) References Cited

OTHER PUBLICATIONS

Gurevitch et al. "Polymerized Pickering HIPEs: Effects of Synthesis Parameters on Porous Structure", Journal of Polymer Science, Part A: Polymer Chemistry, 48: 1516-1525, 2010.
Ikem et al. "High Internal Phase Emulsions Stabilized Solely by Functionalized Silica Particles", Angewandte Chemie, International Edition, 47: 8277-8279, 2008.
Kabiri et al. "Novel Sulfobetaine-Sulfonic Acid-Contained Superswelling Hydrogels", Polymers for Advanced Technologies, 16(9): 659-666, Published Online Aug. 4, 2005.
Kapilov-Buchman et al. "Water-Filled Elastomers Through Droplet Microencapsulation: Release and Degradation", Department of Materials Science and Engineering, Technion—Israel Institute of Technology, Haifa, Israel, Poster, Dec. 31, 2015.
Kapilov-Buchman et al. "Water-Filled Elastomers Through Droplet Microencapsulation: Release and Degradation", Presentation in the Conference IMEC, BarIlan University, Israel, Feb. 1-2, 2016, 17 P., Feb. 2, 2016.
Kovacic et al. "Macroporous Double Network Hydrogels Through Emulsion Templating", Presented at the Polymer Chemistry Gordon Research Conference, Poster, Jun. 30, 2015.
Kovacic et al. "Superabsorbent, High Porosity, PAMPS?Based Hydrogels Through Emulsion Templating", Macromolecular Rapid Communications, 37(22): 1814-1819, Sep. 2016.
Lalani et al. "Electrospun Zwitterionic Poly(Sulfobetaine Methacrylate) for Nonadherent, Superabsorbent, and Antimicrobial Wound Dressing Applications", Biomacromolecules, 13(6): 1853-1863, Apr. 30, 2012.
Laschewsky "Structures and Synthesis of Zwitterionic Polymers", Polymers, 6(5): 1544-1601, May 23, 2014.
Luo et al. "One-Pot Interfacial Polymerization to Prepare PolyHIPEs With Functional Surface", Colloid and Polymer Science, 293(6): 1767-1779, Published Online Mar. 25, 2015.
Madhusudhana et al. "Bicontinuous Highly Cross-Linked Poly(Acrylamide-Co-Ethyleneglycol Dimethacrylate) Porous Materials Synthesized Within High Internal Phase Emulsions", Soft Matter, 7: 10780-10786, Sep. 28, 2011. p. 10781, Left Col., Lines 11-15, PolyHIPES Synthesis Section, p. 10782, Left Col., Lines 28-37, p. 10785, Right Col., Lines 5-8, p. 10786, Left Col., Lines 3-5.
Maji et al. "Dual-Stimuli-Responsive L-Serine-Based Zwitterionic UCST-Type Polymer With Tunable Thermosensitivity", Macromolecules, 48(14): 4957-4966, Jul. 20, 2015.
Menner et al. "High Internal Phase Emulsion Templates Solely Stabilised by Functionalised Titania Nanoparticles", Chemical Communications, p. 4274-4276, 2007.
Menner et al. "Particle-Stabilized Surfactant-Free Medium Internal Phase Emulsions as Templates for Porous Nanocomposite Materials: Poly-Pickering-Foams", Langmuir, 23: 2398-2403, 2007.
Mülhaupt "Catalytic Polymerization and Post Polymerization Catalysis Fifty Years After the Discover of Ziegler's Catalysts", Macromolecular Chemistry and Physics, 204(2): 289-327, Feb. 2003.
Oh et al. "Injectable, Interconnected, High-Porosity Macroporous Biocompatible Gelatin Scaffolds Made by Surfactant-Free Emulsion Templating", Macromolecular Rapid Communications, 36(4): 364-372, Published Online Dec. 10, 2014.
Silverstein "Emulsion-Templated Porous Polymers: A Retrospective Perspective", Polymer, XP028549218, 55(1): 304-320, Available Online Sep. 11, 2013. Abstract, p. 262, Lines 20-22, p. 271, Lines 23-35, p. 273, Lines 10-11, Table S-4.
Silverstein et al. "PolyHIPEs—Porous Polymers From High Internal Phase Emulsions", Encyclopedia of Polymer Science and Technology, p. 1-24, 2010.
Streifel et al. "Porosity Control in High Internal Phase Emulsion Templated Polyelectrolytes Via Ionic Crosslinking", Journal of Polymer Science, Part A: Polymer Chemistry, 54(16): 2486-2492, Published Online Apr. 13, 2016. Abstract, p. 1, col. 1, Lines 6-10.
Tan et al. "Synthesis and Aqueous Solution Properties of Sterically Stabilized PH-Responsive Polyampholyte Microgels", Journal of Colloid and Interface Science, 309: 453-463, Available Online Feb. 16, 2007.
Tobushi et al. "The Influence of Shape-Holding Conditions on Shape Recovery of Polyurethane-Shape Memory Polymer Foams", Smart Materials and Structures, 13:881-887, 2005.
Unknown "Salt Solution-Filled Elastomeric Monoliths Through Templating Within Pickering Emulsions: Release and Degradation", 1 P., Jul. 2016.
Warwar Damouny et al. "Hydrogel-Filled, Semi-Crystalline, Nanoparticle-Crosslinked, Porous Polymers From Emulsion Templating: Structure, Properties, and Shape Memory", Polymer, XP029381315, 82: 262-273, Available Online Nov. 23, 2015.
Yakacki et al. "Strong, Tailored, Biocompatible Shape-Memory Polymer Networks", Advanced Functional Materials, 18(16): 2428-2435, Aug. 22, 2008.
Zhang et al. "Doubly-Crosslinked. Emulsion-Templated Hydrogels Through Reversible Metal Coordination", Polymer, 126: 386-394, Jul. 18, 2017. Esp. Sections 2.2-2.4, Section 3.9.
Zhang et al. "Highly Porous, Emulsion-Templated, Zwitterionic Hydrogels: Amplified and Accelerated Uptakes With Enhanced Environmental Sensitivity", Polymer Chemistry, 9(25): 3479-3487, Published Online May 21, 2018.
Zhang et al. "PMMA Based Foams Made Via Surfactant-Free High Internal Phase Emulsion Templates", Chemical Communications. p. 2217-2219, 2009.
Zheng et al. "Metal-Coordination Complexes Mediated Physical Hydrogels with High Toughness, Stick-Slip Tearing Behavior, and Good Processability", Macromolecules, 49(24), 9637-9646, Dec. 2016.
Zhou et al. "Ion-Responsive Alginate Based Macroporous Injectable Hvdrogel Scaffolds Prepared by Emulsion Templating", Journal of Materials Chemistry B: Materials for Biology and Medicine, 1(37): 4736-4745, Oct. 7, 2013.
Zhu et al. "Monolithic Supermacroporous Hydrogel Prepared From High Internal Phase Emulsions (HIPEs) for Fast Removal of Cu2+ and Pb2+", Chemical Engineering Journal, 284: 422-430, Available Online Sep. 9, 2015.
Notice of Allowance dated Apr. 11, 2022 from US Patent and Trademark Office Re. U.S. Appl. No. 16/747,575. (10 pages).
Yi et al. "Interconnectivity of Macroporous Hydrogels Prepared via Graphene Oxide-Stabilized Pickering High Internal Phase Emulsions", Langmuir, 32(4): 982-990, Jan. 11, 2016.
Final Official Action dated May 2, 2022 from US Patent and Trademark Office Re. U.S. Appl. No. 16/325,401. (16 pages).
Official Action dated Apr. 18, 2022 from US Patent and Trademark Office Re. U.S. Appl. No. 16/629,577. (46 pages).
Polymer Database "Poly(2-Ethylhexyl Acrylate)", Polymer Database, 2 P., 2015.
Interview Summary dated Jul. 18, 2022 from US Patent and Trademark Office Re. U.S. Appl. No. 16/629,577. (2 pages).
Interview Summary dated Jun. 29, 2022 from US Patent and Trademark Office Re. U.S. Appl. No. 16/325,401. (3 pages).
Official Action dated Sep. 30, 2021 from the US Patent and Trademark Office Re. U.S. Appl. No. 16/747,575. (28 pages).
Official Action dated Apr. 9, 2021 From the US Patent and Trademark Office Re. U.S. Appl. No. 16/325,401. (37 Pages).
Official Action dated Oct. 20, 2021 from the US Patent and Trademark Office Re. U.S. Appl. No. 16/325,401. (15 pages).
Interview Summary dated Jul. 23, 2021 from the US Patent and Trademark Office Re. U.S. Appl. No. 16/325,401. (3 ages).

* cited by examiner

FIG. 1
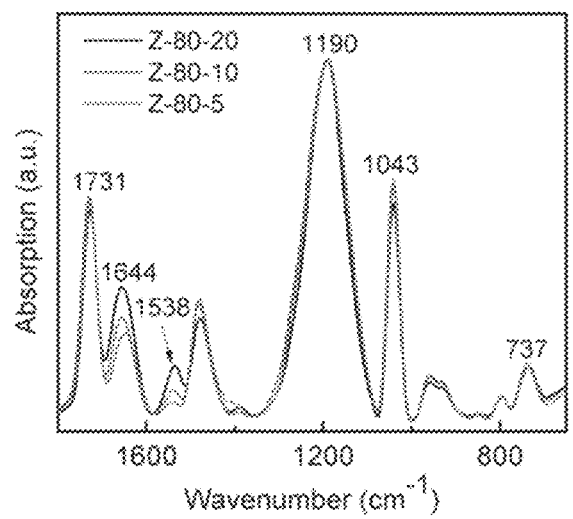
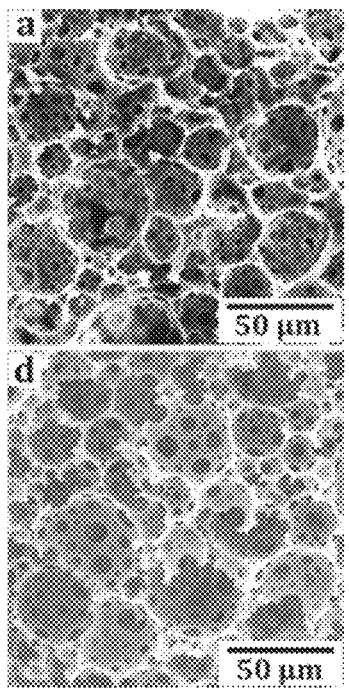
FIG. 2A
FIG. 2D
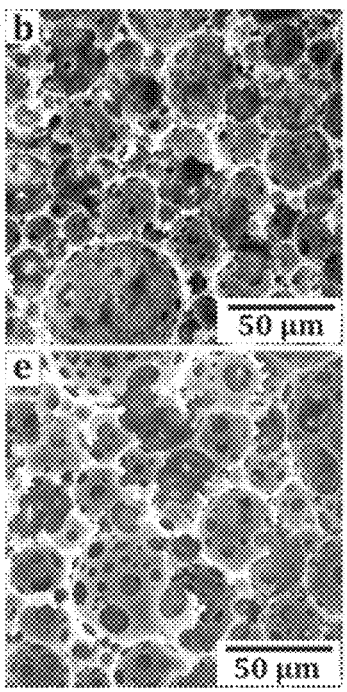
FIG. 2B
FIG. 2E
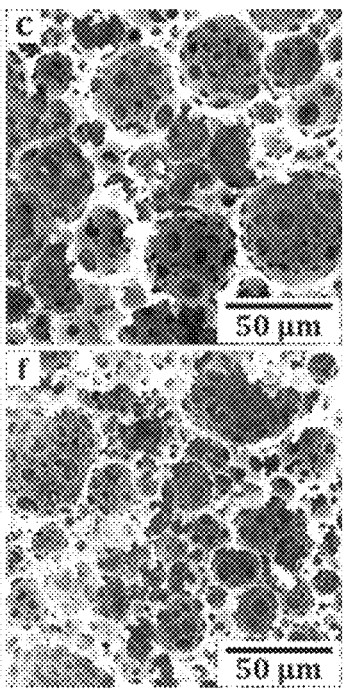
FIG. 2C
FIG. 2F

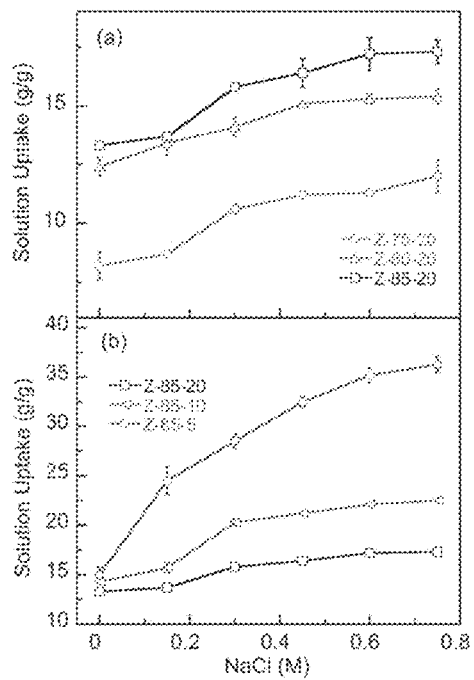
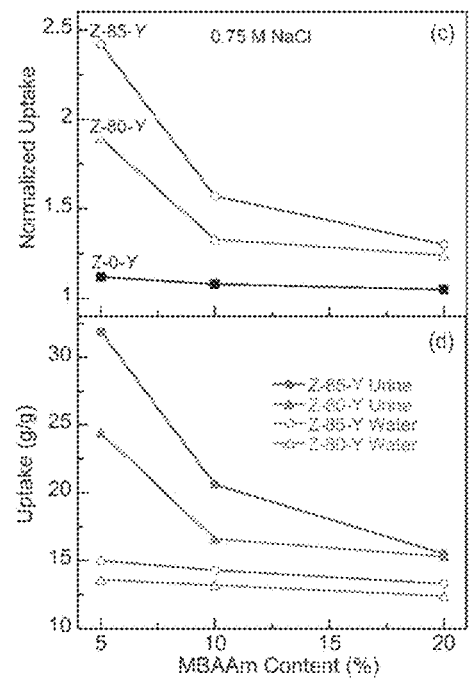
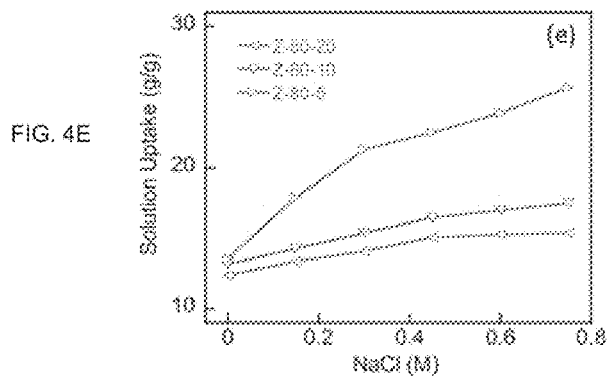
FIG. 4A
FIG. 4B
FIG. 4C
FIG. 4D
FIG. 4E

FIG. 6A
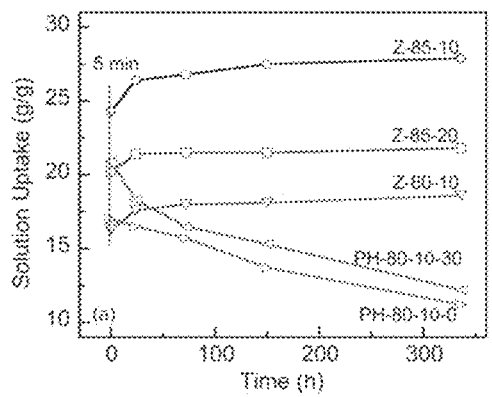
FIG. 6B
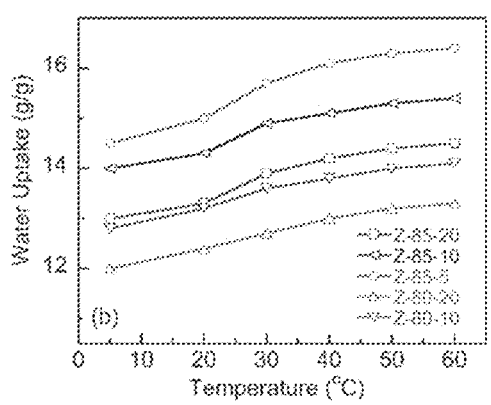
FIG. 6C
FIG. 6D
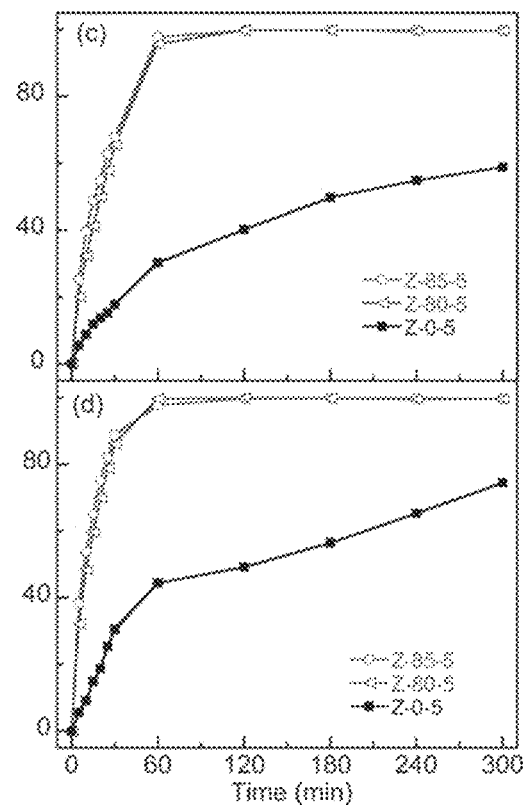

HIPE-TEMPLATED ZWITTERIONIC HYDROGELS, PROCESS OF PREPARATION AND USES THEREOF

RELATED APPLICATIONS

This application is a National Phase of PCT Patent Application No. PCT/IL2018/051158 having International filing date of Oct. 30, 2018, which claims the benefit of priority of Israel Patent Application No. 255404 filed on Nov. 2, 2017. The contents of the above applications are all incorporated by reference as if fully set forth herein in their entirety.

FIELD AND BACKGROUND OF THE INVENTION

The present invention, in some embodiments thereof, relates to composite polymeric materials and, more particularly, but not exclusively, to zwitterionic hydrogels in the form of a polyHIPE, process of preparation and uses thereof.

Zwitterionic polymers, also referred to as polyzwitterions, are specialty polymers with low production volumes so far. Although known at least since the late 1950s, they were considered to be rather exotic compounds. They found a certain interest as ionomers, used in fibers due to strong interactions with charged dye stuffs, and as rheology modifiers in aqueous solutions, due to their high tolerance of highly saline environments. A continuously increasing interest in polyzwitterions began in the 1980s, when they were recognized to be analogs of important biological structures, such as the phospholipids that are the major constituents of cell membranes. Apart from certain alkaloids and hormones such as trigonelline or homarine, other important zwitterionic biological structures are compatible solutes, which are crucial for the osmotic regulation of organisms, such as ectoine or betaine. As a pars pro toto, the name of the latter compound is even frequently used synonymously for polyzwitterions, namely polybetaines.

Zwitterionic hydrogels, hydrogels containing both positive and negative charges on a same pendent group, have drawn considerable attention owing to their widespread practical application including wound dressings, drug delivery, supercapacitors and acid-resistant reactors, wherein the uptake of aqueous solutions, one of the fundamental and principal properties of hydrogels, is essential. The presence of both positive and negative charges on the same repeat unit endows zwitterionic hydrogels with "anti-electrolyte" behavior, behavior which enables them to absorb large amounts of highly concentrated electrolytic solutions. The presence of both positive and negative ionic groups allows zwitterionic hydrogels to interact with the $H^+$ cations at low pH or with the $OH^-$ anions at high pH, making their uptakes highly pH-responsive. The strengths of the intramolecular and intermolecular interactions are influenced by the temperature in zwitterionic hydrogels and can enable temperature-responsive water uptakes.

Despite these advantages, the fabrication of zwitterionic hydrogels with high magnitudes of response and high rates of response remains a challenge. Conventional methods for tuning the properties of zwitterionic hydrogels are based on the copolymerization of different comonomers, the synthesis of new zwitterionic monomers, and the formation of novel physical or chemical networks.

PolyHIPEs (PHs) are emulsion-templated macroporous polymers synthesized within high internal phase emulsions (HIPEs), emulsions containing over 74 vol % dispersed internal phase. The original development of PHs focused upon hydrophobic, crosslinked, amorphous, highly interconnected porous polymers that were templated within the external phases of water-in-oil (w/o) emulsions. Recent work, however, has shown that emulsion templating can be used to synthesize a wide variety of materials systems whose polymerization chemistries, macromolecular structures, and properties are quite different. These very different PH systems include step-growth polymers, semi-crystalline polymers, interpenetrating polymer networks, organic-inorganic hybrids, and closed-cell encapsulating elastomers. Hydrophilic PHs can be generated through the surface functionalization of hydrophobic PHs or through the synthesis of hydrophobic-hydrophilic bicontinuous PHs.

Hydrogel polyHIPEs (HG-PHs), usually generated within oil-in-water (o/w) HIPEs, are of interest for a large number of practical applications ranging from absorption, controlled release, tissue engineering, and enhancing water efficiency in fighting fires. The presence of the highly interconnected, highly porous structure significantly enhances the mechanical properties, the water uptake, and the mass transfer. HG-PHs have been fabricated from non-ionic monomers (including 2-hydroxyethyl methacrylate, acrylamide, N-isopropyl acrylamide, 1-vinyl-5-aminotetrazole, 2-[3-(6-methyl-4-oxo-1,4-dihydropyrimidin-2-yl) ureido]ethyl methacrylate, functionalized glycidyl methacrylate, functionalized biopolymer, and a urea-based deep eutectic) and ionic monomers (including styrene sulfonate, methacrylic acid, sodium acrylate, 2-acrylamido-2-methyl-1-propanesulfonic acid, and [2-(methacryloyloxy)ethyl]trimethylammonium chloride), with recent work reporting HG-PH copolymers with pH-responsive uptakes. The uptakes in HG-PHs were demonstrated to be significantly enhanced by a hydrogel-swelling-driven void expansion mechanism.

Additional prior art documents include "*Polymerized Pickering HIPEs: effects of synthesis parameters on porous structure*" [Gurevitch, I.; Silverstein, M. S., *J. Polym. Sci. A: Polym. Chem.*, 2010, 48, 1516-1525], "*One-Pot Synthesis of Elastomeric Monoliths Filled with Individually Encapsulated Liquid Droplets*" [Gurevitch, I. and Silverstein, M. S., *Macromolecules*, 2012, 45(16), pp. 6450-6456], "*Emulsion-templated porous polymers: A retrospective perspective*" [Silverstein, M. S., *Polymer*, 2014, 55(1), pp. 304-320], "*Emulsion-templated polymers: Contemporary contemplations*" [Silverstein, M. S., *Polymer*, 2017, 126(22), pp. 261-282], Israel Patent Application No. 247302, U.S. Pat. Nos. 8,668,916 and 9,062,245, and U.S. Patent Application Nos. 20090215913 and 20030097103.

SUMMARY OF THE INVENTION

Provided herein are HIPE-templated zwitterionic hydrogels, having unique and heightened absorbate uptake properties compared to bulk zwitterionic hydrogels.

Thus, according to an aspect of some embodiments of the present invention, there is provided a composition-of-matter that includes a polymer, the composition-of-matter is having a microstructure of a polymerized external phase of a high internal phase emulsion (HIPE), wherein the polymer includes a plurality of residues of monomers, at least a portion of which are residues of monomers having a zwitterionic pendant group.

In some embodiments, the polymer is a crosslinked polymer.

In some embodiments, the polymer is crosslinked with a crosslinking agent selected from the group consisting of a poly(ethylene glycol) diacrylate, a poly(ethylene glycol)

dimethacrylate, diethylene glycol diacrylate, diethylene glycol dimethacrylate, ethylene glycol diacrylate, ethylene glycol dimethacrylate, N-(1-hydroxy-2,2-dimethoxyethyl)acrylamide, N,N'-(1,2-dihydroxyethylene)bisacrylamide and N,N'-methylenebisacrylamide (MBAAm).

In some embodiments, the cros slinking level of the crosslinked polymer ranges from 0.01 to 100 mol percent.

In some embodiments, the crosslinking level of the crosslinked polymer ranges from 5 to 20 mol percent.

In some embodiments, the crosslinked polymer is crosslinked with crosslinking agent selected from the group consisting of a modified nanoparticle, a reactive silane, a reactive polyhedral oligomeric silisesquioxane (POSS) and a metal coordination agent.

In some embodiments, the plurality of residues of monomers consisting of the residues of monomers having the zwitterionic pendant group.

In some embodiments, the portion of the plurality of residues of monomers ranges from 1% to 99% of the plurality of residues.

In some embodiments, the zwitterionic pendant group is selected from the group consisting of phosphobetaine, sufobetaine, carboxylbetaine, and their zwitterionic derivatives.

In some embodiments, monomers having the zwitterionic pendant group are selected from the group consisting of an N-substituted acrylamide sulfobetaine, 1-(3-sulfopropyl)-2-vinylpyridinium hydroxide inner salt, 3-sulfopropyldimethyl-3-methacrylamidopropylammonium inner salt, 1-(4-vinylpyridin-1-ium-1-yl)propane-1-sulfonate, 2-methacryloyloxyethyl phosphorylcholine, 3-(1-vinyl-1H-imidazol-3-ium-3-yl)propane-1-sulfonate, carboxybetaine acrylamide, N-(3-sulfopropyl)-N-(methacryloxyethyl)-N,N-dimethylammonium betaine (SBMA), and their zwitterionic derivatives.

In some embodiments, the plurality of residues of monomers includes residues of water-soluble monomers having a negatively charged pendant group, monomers having a positively charged pendant group, and/or monomers having a non-ionic pendant group.

In some embodiments, the plurality of residues of monomers includes residues of water-soluble monomers having a negatively charged pendant group.

In some embodiments, monomers having a negatively charged pendant group are selected from the group consisting of acrylic acid, methacrylic acid, 2-acrylamido-2-methyl-1-propanesulfonic acid (PAMPS), 2-carboxyethylacrylate, 2-methyl-2-propene-1-sulfonic acid, 2-propene-1-sulfonic acid, 2-sulfoethyl methacrylate, 3-butene-1,2,3-tricarboxylic acid, 3-sulfopropyl methacrylate, 4,4-Bis(4-hydroxyphenyl)pentanoic acid, 4-styrenesulfonic acid, 4-vinylbenzoic acid, bis(2-methacryloxyethyl)phosphate, bisacrylamidoacetic acid, itaconic acid, monoacryloxyethyl phosphate, styrene sulfonate (4-vinylbenzenesulfonate), vinylsulfonic acid, and their salts and negatively charged derivatives.

In some embodiments, the plurality of residues of monomers that includes negatively charged residues, is substantially devoid of residues of positively charged monomers.

In some embodiments, the plurality of residues of monomers includes residues of water-soluble monomers having a positively charged pendant group.

In some embodiments, monomers having the positively charged pendant group are selected from the group consisting of (3-acrylamidopropyl)trimethylammonium chloride, (vinylbenzyl)trimethylammonium chloride, [2 (methacryloyloxy)ethyl]trimethylammonium chloride, [3(methacryloylamino)propyl]trimethylammonium chloride, 1-vinyl-5-aminotetrazole, 2-(dimethylamino)ethyl acrylate, 2-(dimethylamino)ethyl methacrylate, 2 [3 (6 methyl 4-oxo-1,4-dihydropyrimidin-2-yl)ureido] ethyl methacrylate, 2 methacryloxyethyltrimethylammonium chloride, 3 methacryloxy 2 hydroxypropyltrimethylammonium chloride, diallyldimethylammonium chloride, 2 acryloxyethyltrimethylammonium chloride, and their salts and positively charged derivatives.

In some embodiments, the plurality of residues of monomers that includes positively charged residues, is substantially devoid of residues of negatively charged monomers.

In some embodiments, the plurality of residues of monomers includes residues of water-soluble non-ionic monomers.

In some embodiments, water-soluble non-ionic monomers are selected from the group consisting of a hydroxy alkyl cellulose, a poly(ethylene glycol) acrylate, a poly (ethylene glycol) methacrylate, a polyoxazolidone, a polyvinyl methyl ether, an N,N-dialkylacrylamide, 2-hydroxyethyl acrylate, 2-hydroxyethyl methacrylate, acrylamide, diacetone acrylamide, dimethylaminoethyl methacrylate (DMAEMA), glycidyl methacrylate, N-(1-hydroxy-2,2-dimethoxyethyl)acrylamide, N,N-dimethylacrylamide, N-[3-(dimethylamino)propyl]methacrylamide, N-acryloylpyrrolidine, N-alkylacrylamide, N-hydroxyethyl acrylamide, N-isopropyl acrylamide, N-vinylimidazoline, polyethlyene oxide, polymethacrylic acid, styrene, vinyl acetate, and their water-soluble non-ionic derivatives.

In some embodiments, the HIPE includes an internal organic phase and an external aqueous phase, the external aqueous phase being a pre-polymerization mixture that includes a plurality of monomers.

In some embodiments, the organic internal phase constitutes from 40 percent to 95 volume percent of the HIPE.

In some embodiments, the internal organic phase includes a water-immiscible solvent or melt selected from the group consisting of hexane, toluene, cyclohexane, pentane, heptane, octane, decane, benzene, xylene and octadecane.

In some embodiments, the HIPE further includes and a crosslinking agent, a HIPE-stabilizing agent and a polymerization initiator.

In some embodiments, the HIPE-stabilizing agent is selected from the group consisting of a surfactant, a block copolymer, a modified inorganic nanoparticle and a modified organic nanoparticle.

In some embodiments, the surfactant is a non-ionic surfactant selected from the group consisting of a poloxamer, an alkylphenol hydroxypolyethylene, a polyethoxylated sorbitan ester, sorbitan monooleate, polyglycerol polyricinoleate, a hydrophobic-hydrophilic block copolymer, and any combination thereof.

In some embodiments, the composition-of-matter presented herein is characterized by a dry density that ranges from 0.03 g/cm3 to 0.6 g/cm3.

In some embodiments, the composition-of-matter presented herein is characterized by exhibiting an anti-polyelectrolyte effect, wherein an uptake of a solution of an ionic solute at a first concentration is higher than the uptake at a second concentration, the first concentration is higher than the second concentration.

In some embodiments, the composition-of-matter presented herein is characterized by exhibiting a pH-responsive solution uptake, wherein an uptake of a solution having a pH below or above an isoelectric point of the composition-of-matter is higher than the uptake at the isoelectric point.

In some embodiments, the composition-of-matter presented herein is characterized by exhibiting a temperature-responsive solution uptake, wherein an uptake of a solution at a first temperature is higher than the uptake at a second temperature, the first temperature is lower than the second temperature.

According to an aspect of some embodiments of the present invention, there is provided a hydrogel that includes the composition-of-matter of any one of claims 1-28, and an aqueous medium absorbed therein.

In some embodiments, the aqueous medium is water, an aqueous solution of an ionic solute, an aqueous acid solution, an aqueous base solution, waste-water, and urine.

According to an aspect of some embodiments of the present invention, there is provided an article of manufacturing includes the composition-of-matter presented herein.

In some embodiments, the article of manufacturing is selected from the group consisting of a basic solution retention device, an acidic solution retention device, a cosmetic product, a diaper, a filter material, matrix or device, a flood/spill control material or device, a grooming product, a liquid waste material or device, a personal care and/or hygiene product, a surgical pad, a water purification material, matrix or device, a water retention material or containing device, a wound dressing, an incontinence garment, and an ion-exchange material, matrix or device.

According to an aspect of some embodiments of the present invention, there is provided a process of preparing the composition-of-matter presented herein, the process includes subjecting a high internal phase emulsion (HIPE), having an internal organic phase and a polymerizable external aqueous phase, to polymerization of the polymerizable external aqueous phase, wherein the internal organic phase includes a water-immiscible solvent, and the polymerizable external aqueous phase includes a plurality of monomers and at least one crosslinking agent, at least a portion of the monomers is having a zwitterionic pendant group.

In some embodiments, the plurality of monomers consisting of monomers having a zwitterionic pendant group.

In some embodiments, the portion of zwitterionic monomers in the polymerizable external aqueous phase ranges from 1% to 99% of said plurality of monomers.

In some embodiments, the plurality of monomers may further include water-soluble monomers having a negatively charged pendant group, water-soluble monomers having a positively charged pendant group, and water-soluble monomers having a non-ionic pendant group.

In some embodiments, the HIPE includes a HIPE-stabilizing agent.

In some embodiments, the process further includes, prior to subjecting the polymerizable external phase to polymerization, forming the HIPE by mixing the internal organic phase and the polymerizable external aqueous phase.

In some embodiments, the process further includes, subsequent to forming the HIPE, adding a polymerization initiator to the HIPE.

In some embodiments, the volume fraction of the internal organic phase in the HIPE ranges from 0.4 to 0.95.

In some embodiments, the process further includes, subsequent to polymerization of the HIPE, substantially removing the internal organic phase from the composition-of-matter.

In some embodiments, removing the internal phase includes exchanging the water-immiscible organic solvent or melt with a water-miscible organic solvent.

In some embodiments, exchanging the water-immiscible organic solvent with a water-miscible organic solvent is effected by immersion.

In some embodiments, the immersion is effected at a temperature lower than 0° C.

In some embodiments, the water-miscible organic solvent is selected from the group consisting of an alcohol, ethanol, methanol, acetone, acetonitrile, N,N-dimethylformamide (DMF) and dimethylsulfoxide (DMSO).

In some embodiments, process further includes, subsequent to exchanging the internal phase, subjecting the composition-of-matter to extraction in the water-miscible organic solvent, and drying the composition-of-matter from the water-miscible organic solvent.

According to an aspect of some embodiments of the present invention, there is provided a composition-of-matter, as presented herein, prepared by the process presented herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying figures. With specific reference now to the figures in detail, it is stressed that the particulars shown are by way of example and for purposes of illustrative discussion of embodiments of the invention. In this regard, the description taken with the figures makes apparent to those skilled in the art how embodiments of the invention may be practiced.

In the drawings:

FIG. 1 presents an FTIR spectra of the Z-80-Y samples, normalized using the peak height at 1190 cm$^{-1}$;

FIGS. 2A-F present the porous structures of the Z-80-Y and Z-85-Y samples as seen in SEM micrographs, wherein FIG. 2A shows the Z-80-20 sample, FIG. 2B shows the Z-80-10 sample, FIG. 2C shows the Z-80-5 sample, FIG. 2D shows the Z-85-20 sample, FIG. 2E shows the Z-85-10 sample, and FIG. 2F shows the Z-85-5 sample;

FIGS. 4A-E present comparative plots of NaCl solution uptake as a function of NaCl concentration by various samples: Z-X-20 (FIG. 4A), Z-85-Y (FIG. 2B), and the effect of the MBAAm content on the uptake: uptake of a 0.75 M NaCl solution normalized by the uptake of water (FIG. 4C), uptake of water and artificial urine (FIG. 4D), and uptake of NaCl solutions by the Z-80-Y samples (FIG. 4E);

FIGS. 6A-D present comparative plots showing variation in the uptake of a 6 M HCl solution as a function of time (FIG. 6A), the effects of temperature on the water uptake (FIG. 6B), the relative increase in uptake upon immersing water-swollen zwitterionic hydrogels in a 0.75 M NaCl solution (FIG. 6C) and in water at pH 10 (FIG. 6D).

DESCRIPTION OF SPECIFIC EMBODIMENTS OF THE INVENTION

Figure 3A:
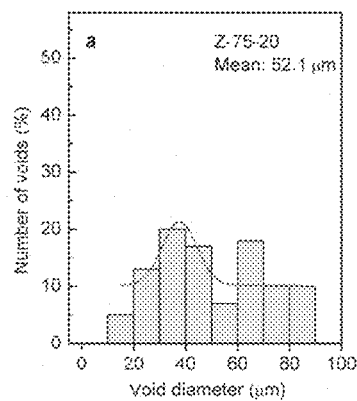
FIGS. 3A-G show the void diameter distribution in sample Z-75-20 (FIG. 3A), sample Z-80-20 (FIG. 3B), sample Z-80-10 (FIG. 3C), sample Z-80-5 (FIG. 3D), sample Z-85-20 (FIG. 3E), sample Z-85-10 (FIG. 3F), and sample Z-85-5 (FIG. 3G)
Figure 3B:
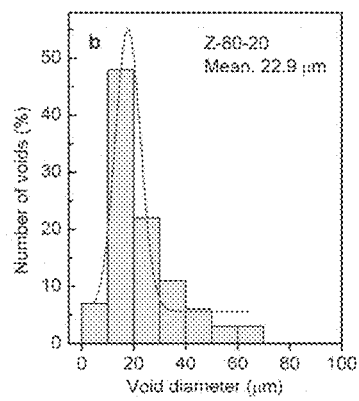
Figure 3C:
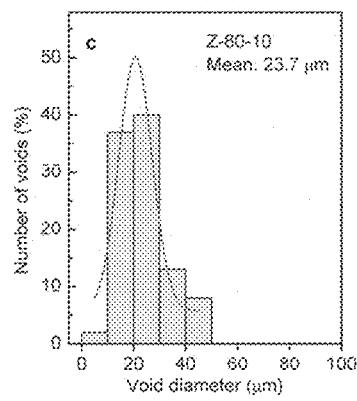
Figure 3D:
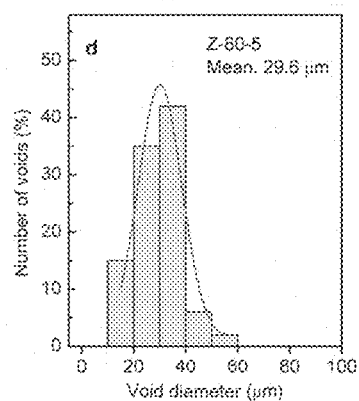
Figure 3E:
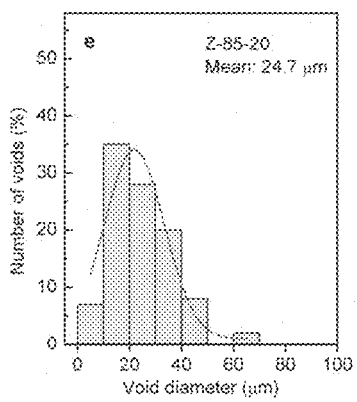
Figure 3F:
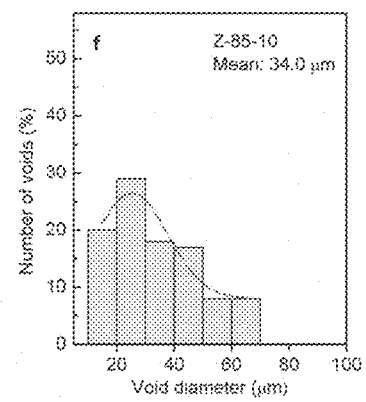

The present invention, in some embodiments thereof, relates to composite polymeric materials and, more particularly, but not exclusively, to zwitterionic hydrogels in the form of a polyHIPE, process of preparation and uses thereof.

The principles and operation of some embodiments of the present invention may be better understood with reference to the figures and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While conceiving the present invention, the present inventors have envisioned that emulsion templating may enhance the water uptakes of zwitterionic hydrogels, and that in the form of a polyHIPE, such HGs may be tunable in both the magnitudes and the rates of their response to pH. However, as known in the art, zwitterionic monomers are fundamentally different from conventional ionic monomers since both the positive and negative charges are fixed and present on the same molecule; hence, HIPEs in principle, and polyHIPEs containing zwitterionic monomers are not trivial to achieve.

While reducing the present invention to practice, it was surprisingly found that, under certain conditions, a new class of polyHIPE hydrogels comprising zwitterionic polymers, referred to herein as zwitterionic HG-PHs, or Z-HG-PHs for short, can be fabricated. As presented hereinbelow, exemplary Z-HG-PHs were studies for their multi-responsive uptakes. These exemplary Z-HG-PHs were synthesized within o/w HIPEs through the polymerization of a commercially available zwitterionic monomer, N-(3-sulfopropyl)-N-(methacryloxyethyl)-N,N-dimethylammonium betaine (SBMA) and crosslinked using N,N'-methylenebisacrylamide (MBAAm) (Scheme 1).

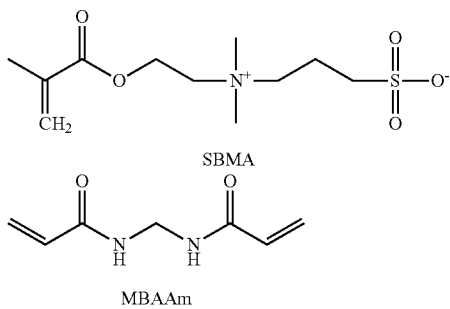

Scheme 1

While further reducing the present invention to practice, it was found that the water uptakes of the interconnected macroporous Z-HG-PHs, could be tuned by varying both the dispersed phase content and the crosslinking comonomer content. The anti-electrolyte effect, the dual pH-responsive uptakes, and the temperature-responsive uptakes were amplified, the responses were accelerated, and the sensitivity to the environment was enhanced by the macroscopic structure of the HIPE-templated zwitterionic hydrogels. These Z-HG-PHs exhibited high chemical stability, absorbing relatively large amounts of a 6 M HCl solution, properties needed for the absorption and storage of such solutions.

HIPE-Templated Compositions-of-Matter:

As known in the art and presented hereinabove, high internal phase emulsions (HIPEs) are concentrated systems of water-in-oil, oil-in-water, or oil-in-oil possessing a large volume of the internal, or dispersed phase, with a volume fraction of over 0.74, resulting in the deformation of the dispersed phase droplets into polyhedra or in the formation of a polydisperse droplet size distribution. The dispersed droplets are separated by thin films of the continuous phase. As HIPEs are intrinsically unstable, the HIPE is typically stabilized by adding an emulsion stabilizer to either the external phase and/or the internal phase; this stabilizer is referred to herein as a HIPE-stabilizing agent.

As discussed hereinabove, polymer materials can be prepared from HIPEs if one or the other (or both) phases of the emulsion contain polymerizable species, also referred to herein as monomers, comonomers and monomeric units. This process yields a range of foam-like products with widely differing properties. As the concentrated emulsion acts as a scaffold or template, the microstructure of the resultant material is determined largely by the HIPE's structure immediately prior to polymerization and through changes that may occur during polymerization and/or during post-polymerization processing.

According to some embodiments of the present invention, the composition-of-matter is characterized, and therefore can be structurally identified, by its microstructure, which is structurally templated by a high internal phase emulsion (HIPE). A polyHIPE, which is the result of subjecting the HIPE to polymerization, is a continuous polymer envelope surrounding the dispersed droplets of the internal phase. A polyHIPE results if the continuous, external phase contains polymerizable monomers; if the internal phase is the polymerizable phase, and the external phase is not polymerizable, the result of a polymerization process will not be a polyHIPE; a concentrated latex results if only the discrete, internal phase contains polymerizable monomers. The composition-of-matter presented herein comprises a continuous polymeric matrix, which is the product of a polymerized external phase of a HIPE. Thus, the continuous polymeric matrix of the composition-of-matter presented herein includes a polymeric polyHIPE having the shape and microstructure of the predecessor HIPE. In other words, by having a microstructure of a polyHIPE, it is meant that the microstructure of the composition-of-matter presented herein results from a polymerization process that occurs within a HIPE.

The composition-of-matter presented herein is said to be "HIPE-templated", namely its microstructure is a projection of the microstructure of a HIPE before and after its polymerization. Briefly, a HIPE is a plurality of tightly-packed substantially spheroidal and/or polyhedral droplets of various sizes, constituting the dispersed internal phase, separated by walls of a liquid constituting the continuous external phase. The average size and size distribution of the droplets is controlled by the chemical composition and mechanical treatment of the emulsion phases, and are typically characterized by a population of one or more narrowly distributed sizes. For example, average droplet size and distribution can be controlled by use of emulsion stabilizers (surfactants, surface-active substances, solid particles etc.), which may act to reduce the tendency of the droplets to coalesce.

The term "polyHIPE" can therefore be used as a structural term to describe a highly porous monolithic structure of thin walls separating a collection of tightly-packed voids, referred to herein as the "matrix". The walls are typically thinner at the closest distance between what was tightly-packed droplets before polymerization, and thicker at the spaces between adjacent droplets. When a HIPE is polymerized to yield a polyHIPE, the same microstructure is substantially preserved. The polymerization of the continuous phase of a HIPE "locks in" the HIPE's droplets before any destabilization through droplet coalescence and/or Ostwald ripening can occur; in some cases, the droplets are locked in closed cells, and in some cases the cells are interconnected.

Hence, the phrases "having a microstructure of a polymerized external phase of a high internal phase emulsion (HIPE)", "structurally-templated by an external phase of a high internal phase emulsion (HIPE)", or the term "HIPE-templated", are equivalent expressions of a structural definition rather than a process-related expressions, since they relate the microstructure of the HIPE to the microstructure of the resulting matrix of the composition-of-matter, which is no longer an emulsion but a solid matter, referred to in the context of the present embodiments as a polyHIPE or a continuous elastomeric matrix, or simply as a "matrix".

In some instances, the thinnest areas some of the walls give way to interconnecting windows connecting droplets in adjacent voids, thereby forming an open-cell microstructure. In the case of open-cell polyHIPEs, when the polyHIPE is dried and the dispersed phase is removed, the droplets leave empty voids in their place, which are interconnected by the windows in the walls, wherein the voids can be referred to as having an open-cell microstructure.

According to some embodiments of the present invention, the microstructure of the polymeric compositions-of-matter is structurally-templated by an oil-in-water (o/w) high internal phase emulsion. In some embodiments, the internal organic phase comprises a water-immiscible solvent, or a melt (a molten low-temperature melting point organic substance; melting point 20-100° C.), such as, without limitation, hexane, toluene, cyclohexane, pentane, heptane, octane, decane, benzene, xylene, octadecane and mixtures thereof.

By definition, a HIPE exhibits at least 74% internal phase, although originally it was defined as 70%. When using emulsion templating to produce porous monolithic medium internal phase emulsions (MIPEs) the internal phase content ranges from 30% to 74%, or by some definitions from 50% to 70%, and low internal phase emulsions (LIPE) contain internal phase contents that are less than 30% (or by some definitions less than 50%). In the context of embodiments of the present invention, unless stated otherwise, the term "HIPE-templated elastomer/polymer" encompasses, at least in the sense of the structural definition, the microstructure of HIPE-, MIPE- and LIPE-templated microstructures, wherein the lower the internal phase content, the thicker the walls and the better the encapsulation thereof in the elastomer/polymer. In some embodiments of the present invention, the organic internal phase of the HIPE preceding the polyHIPE, constitutes from 40 percent to 95 volume percent of the HIPE, or in other words, the volume fraction of the organic polymerizable external phase in the HIPE ranges from 0.4 to 0.95. Once polymerized, cleaned-of the internal phase and dried, the composition-of-matter presented herein is characterized by a dry density that ranges from 0.03 g/cm$^3$ to 0.6 g/cm$^3$, demonstrating its highly porous microstructure.

As used herein, the term "continuous" refers to a macroscopic as well as a microscopic property of the matrix forming a part of the composition-of-matter presented herein. According to some embodiments of the present invention, the polymeric matrix is a continuous mass of the polymer or a connected assembly or aggregate of discrete bodies, as opposed to an assembly or aggregate of discrete bodies which are discontinuous with respect to one-another even if these are in direct contact with one-another. Hence, in the context of embodiments of the present invention, the phrase "continuous polymeric matrix" refers to a continuous mass of a polymeric substance.

It is noted herein that in some embodiments, the internal phase may be a melt of a room temperature solid, as in the case of some a phase-change materials (PCM), which may be found in the liquid state at moderately elevated temperatures (30-100° C.), particularly at the temperature at which the HIPE is prepared and possibly when it is polymerized. Nonetheless, as long as it was in the liquid form during the formation of the precursor HIPE, in the context of embodiments of the present invention, it is referred to herein as a liquid even if it is a solid at room temperature.

Zwitterionic Monomers and Polymers:

The composition-of-matter presented herein comprises a zwitterionic polymer; therefore, the composition-of-matter includes a HIPE-templated zwitterionic polymeric matrix that includes a zwitterionic polymer or at least includes residues of a zwitterionic monomer. The terms "zwitterionic polymer" and "polyzwitterion", used herein interchangeably (and also known in the literature as "polybetaine"), refer to a class of polymers that bear, within their constitutional repeat unit (i.e., within the residue of a monomer in the polymer), the same number of anionic and cationic groups, which are essentially functional over a large pH-window. Accordingly, the overall charge of polyzwitterions is zero under normal conditions, notwithstanding that they are characterized by a high density of polymer-bound ion pairs attached to the polymer chain. Thus, polyzwitterions (left illustration in Scheme 2) represent a special subclass of polyampholytes, featuring particular properties that are different than most polycations and/or polyanions polyelectrolytes (right illustration in Scheme 2); the latter polymer class carries simultaneously anionic and cationic groups, too, yet there is a priori no particular mutual correlation between them.

Scheme 2

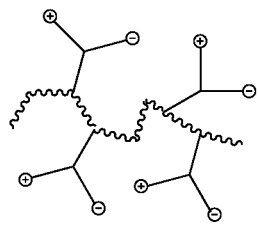

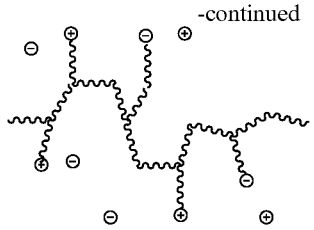

As can be seen in Scheme 2, in a pure polyampholytes, anionic and cationic sites may be scattered at random along the polymer chains, one charged species may outnumber the other one (often by far), and one (or even both) of the charged species may be present only in a narrow pH-range. Hence, polyampholytes typically bear an overall net charge (except for a specific narrow pH range, where the number of cationic and anionic sites may be equal, thus behaving like polyzwitterions). The net charge can be positive or negative, and may sensitively vary with the pH and ionic strength of the system studied, with respect to the absolute amount as well as the change of the sign. Therefore, polyampholytes behave mostly either as polyanionic or as polycationic species, whereas pure polyzwitterions (polymers consisting of residues of monomers having a zwitterionic pendant group) due to their overall charge neutrality exhibit a different, hybrid-like property profile. On the one hand, strong Coulomb interactions prevail in polyzwitterions, which thus generally exhibit high hydrophilicity; while on the other hand, polyzwitterions do not show the typical polyelectrolyte effects, but their behavior shares many similarities with polar non-ionic polymers.

In the context of embodiments of the present invention, polyzwitterions should be also clearly distinguished from other polymer classes such as mesoionic polymers and polymeric ylides; polymers comprising monomeric residues presenting a mesoionic or an ylide pendant group, respectively. Mesoionic compounds can be only presented by canonical formulas via a set of mesomeric structures that contain formally cationic and anionic sites; yet, they do not carry separate charges but dispose only of a high dipole moment. Generally, they are not even effective hydrophilic groups. Ylides are 1,2-dipolar compounds with a semi-polar bond, which may be represented by canonical formulas with formally separate positive and negative charges on neighboring atom; yet, ylide moieties typically exhibit a high double bond character and a low hydrophilicity as well.

In the context of the present invention, the polymer comprising the HIPE-templated matrix, can be defined structurally by the molar percentage (relative number) of residues of monomers that bear a zwitterionic pendant group in the entire polymer (the total number of residues in the polymer). In some embodiments, the zwitterionic polymer consists of residues of monomers having a zwitterionic pendant group (100% zwitterionic monomers; zwitterionic homopolymer). In some embodiments, at least a portion the polymer is made of zwitterionic monomers, while the rest is made of ionic and and/or non-ionic monomers, including mesoionics and ylides (1% to 99.9% zwitterionic copolymer; having from 1% to 99.9% residues of monomers having a zwitterionic pendant group).

Scheme 3 illustrates the various possibilities to implement ion pairs within monomeric residues in polymers, in order to produce polyzwitterions.

Scheme 3

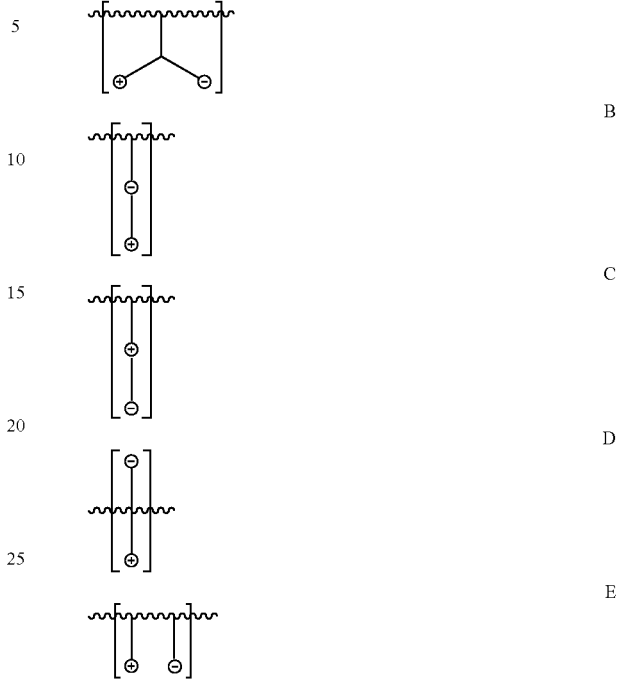

With the exception of type E in Scheme 3, types A-D are examples of polymers having residues of monomers characterized by possessing a zwitterionic pendant group, whereas type D is encompassed under the definition of a zwitterionic pendant group although it presents two pendant groups in the same residue. Type E is an example of a polyelectrolyte.

Scheme 4 presents exemplary zwitterionic pendant groups which are encompassed by some embodiments of the present invention as forming a part of the composition-of-matter provided herein, and which also have been practically incorporated in polymers: ammoniophosphates (phosphobetaines or lecithin analogues) I and XIV, ammoniophosphonates (phosphonobetaines) II, IV and XV, ammoniophosphinates (phosphinobetaines) III, ammoniosulfonates (sulfobetaines) V and XVI, ammoniosulfates VI and XVII, ammoniocarboxylates (carbo- or carboxybetaines) VII, X, XI, XVIII and XXI, ammoniosulfonamides VIII, ammonisulfon-imides IX, guanidiniocarboxylates (asparagine analogs) X, pyridiniocarboxylates XI, ammonio(alkoxy)dicyanoethenolates XII, ammonioboronates XIII, sulfoniocarboxylates XIX, phosphoniosulfonates XX, phosphoniocarboxylates XXI, squaraine dyes XXII, oxypyridine betaines XXIII and XXIV; wherein R represents an alkyl moiety.

Scheme 4

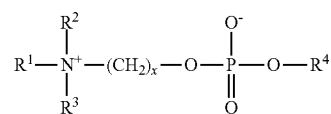

I

-continued

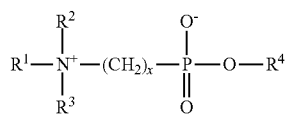
II

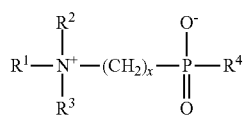
III

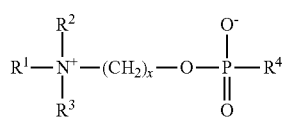
IV

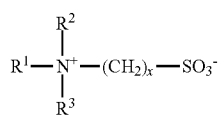
V

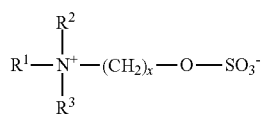
VI

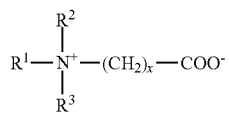
VII

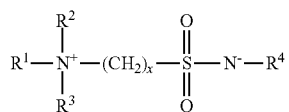
VIII

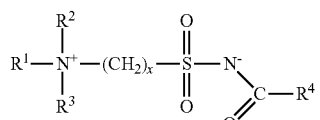
IX

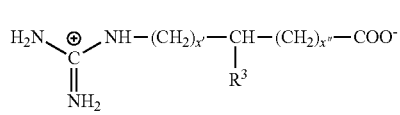
X

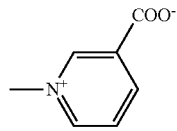
XI

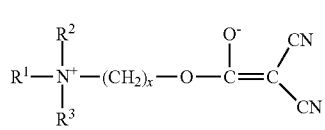
XII

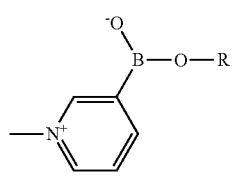
XIII

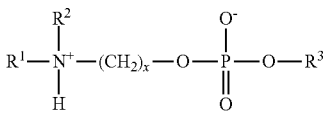
XIV

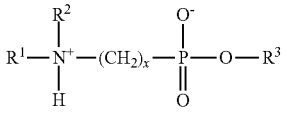
XV

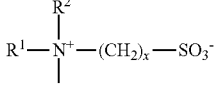
XVI

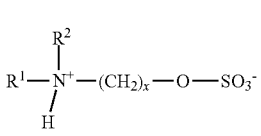
XVII

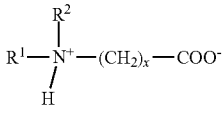
XVIII

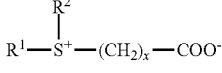
XIX

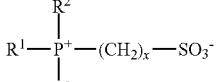
XX

XXI

XXII

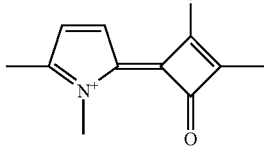
XXIII

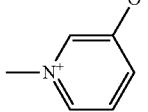
XXIV

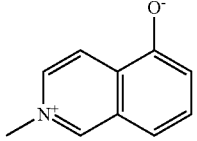

In some embodiments, the monomers being polymerized into the composition-of-matter provided herewith include, without limitation, an N-substituted acrylamide sulfobetaine, 1-(3-sulfopropyl)-2-vinylpyridinium hydroxide inner salt, 3-sulfopropyldimethyl-3-methacrylamidopropylammonium inner salt, 1-(4-vinylpyridin-1-ium-1-yl)propane-1-sulfonate, 2-methacryloyloxyethyl phosphorylcholine, 3-(1-vinyl-1H-imidazol-3-ium-3-yl)propane-1- sulfonate, carboxybetaine acrylamide, N-(3-sulfopropyl)-N-(methacryloxyethyl)-N,N-dimethylammonium betaine (SBMA), [2-(methacryloyloxy)ethyl] dimethyl-(3-sulfopropyl) ammonium hydroxide (SBA), and their zwitterionic derivatives.

Additional information regarding zwitterionic monomers and their polymerization can be found in reviews such as "*Structures and Synthesis of Zwitterionic Polymers*" by André Laschewsky, *Polymers* 2014, 6, pp. 1544-1601.

Crosslinking Agents:

In some embodiments, the zwitterionic polymer of the composition-of-matter presented herein, is a hydrogel. The term "hydrogel", as used herein, refers to a gel in which the liquid is an aqueous medium, or water. In the context of the present invention, a gel or a hydrogel is a network of crosslinked polymeric strands, or simply a crosslinked polymer.

In the context of the present invention, any agent that can link two or more polymeric strands is a crosslinking agent. A crosslinking agent can be a hub of several polymeric strands, or a link between two polymeric strands. Crosslinking may be effected via main-chain atoms or via pendant group atoms, or both. A crosslinking agent is also characterized according to its capacity to alter the elasticity/rigidity balance of a polymeric composition. Thus, a crosslinking agent (or moiety) is a component having an effect on the flexibility of the obtained polymer, giving it the desired mechanical properties. Crosslinks bond one polymer chain to another by covalent bonds, coordinative bonds or ionic bonds. When the term "crosslinking" is used in the synthetic polymer science field, it usually refers to the use of crosslinks to promote a difference in the polymer's physical properties.

As used herein, the phrases "crosslinking agent" refers to a substance that promotes or regulates intermolecular covalent, ionic, hydrogen, coordinative, hydrophobic or other form of bonding between polymer chains, linking them together to create a network of chains which result in a more cohesive structure. Crosslinking agents, monomers or oligomers, having a plurality of polymerizable moieties attached thereon, according to some embodiments of the present invention, contain a functionality greater than two, for example, two double bonds (vinyls) (a functionality of four) or three amines (a functionality of three), creating chemical bonds between two or more polymer molecules (chains).

Crosslinking agents include, without limitation, crosslinking comonomers (molecules that participate in the polymerization process and contribute reactive functional groups to the main-chain), nanoparticles modified to present a plurality of reactive functional groups thereon, such as reactive silanes, and reactive polyhedral oligomeric silisesquioxanes (POSS), multi-functional oligomers, and metal coordination agent. The type of crosslinking agent is selected according to its compatibility with the other polymerizable units, the HIPE-forming conditions, and the conditions of the HIPE polymerization reaction. The crosslinking agent is also selected according to its solubility, wherein a crosslinking agent that can dissolve in the pre-polymerizable mixture together with the monomers will be a natural choice, while crosslinking agents that can dissolve in the other phase but can cross the phase boundary during the polymerization process are also contemplated. For example, ethylene glycol dimethacrylate (EGDMA) is hydrophobic and can dissolve more readily in the internal organic phase, and it is contemplated as a crosslinking agent since it has been shown to take part in a polymerization reaction of an emulsion that occurs in the aqueous phase.

Most polyHIPEs are crosslinked using crosslinking comonomers such as divinylbenzene (DVB) for w/o-based polyHIPEs and N,N'-methylenebisacrylamide (MBAAm) for o/w-based polyHIPEs. A crosslinking comonomer, in the abovementioned example of radical polymerization, is a molecule with at least two polymerizable double bonds. The most common crosslinking comonomers contain two polymerizable double bonds. However, it is also possible to crosslink polyHIPEs using comonomers or oligomers containing multiple polymerizable double bonds, or other reactive functional groups in other polymerization mechanisms, such as carboxyls, ethers, cyanates, amines, amides, sulfones, sulfates, thiols, hydroxyls and the likes.

As presented in U.S. Pat. No. 9,062,245 and elsewhere, stabilizing NPs bearing polymerizable double bonds can also function as crosslinking centers (hubs). The silane functionality can contain such bonds. The crosslinking using NPs affected the microstructure of the resulting polyHIPE compared to crosslinking using non-interfacial crosslinking comonomers. Since the Pickering HIPE NPs are located at the oil-water interface before polymerization, it has been expected that they will be found on the void surfaces in the polyHIPE (the phase interface), rather than in the bulk of the polymer (not necessarily at or near the phase interface); however, the NPs may also end up being within the walls, pushed from the interface by monomer diffusion, and not on the void surface. Interfacial crosslinking may increase the elastomeric nature since there are often less crosslinking sites than exist when using a non-interfacial crosslinking agent.

Monomers and oligomers useful as polymerizable moieties, according to some embodiments of the present invention, may be represented as being a monomer or oligomer containing a vinyl group (e.g., ethylene, propylene, vinyl chloride, vinyl acetate, acrylates, methacrylates, styrenes, dienes) or a vinylidene group having the structural formula $CH_2=C<$ where at least one of the disconnected valences is attached to an electronegative radical such as phenyl, acetoxy, carboxy, carbonitrile and halogen, examples of the monomers being those hereinbefore listed as well as styrene, vinylnaphthalene, alphamethylstyrene, dichlorostyrenes, alpha-methylene carboxylic acids, their esters, nitriles and amides including acrylic acid, acrylonitrile, acrylamide; the vinyl esters of alkanoic acids including vinyl formate, vinyl acetate, vinyl propionate, vinyl butyrate, vinyl pyridine; the alkyl vinyl ketones including methyl vinyl ketone; the conjugated diolefines including 1,3-butadiene; isoprene chloroprene, piperylene and 2,3-dimethyl-1,3-butadiene $(CH_2=C(CH_3)C(CH_3)=CH_2)$.

Additional monomers and oligomers useful as polymerizable moieties, according to some embodiments of the present invention, include, without limitation, ring-opening monomers and oligomers such as lactams, lactones, cyclic ethers and epoxides; condensation monomers such as di-carboxylic acids, di-acylhalides, diamines, di-amides, di-esters, diketones, amino-acids, polyols and the likes.

According to embodiments of the present invention, the polymer is crosslinked into a network using reactive oligomers to crosslink the monomers (oligomers as crosslinking agents). In the context of embodiments of the present invention, the term "oligomer" refers to reactive oligomers, thereby emphasizing that they can participate as reactive species in the polymerization reaction as comonomers and/or crosslinking agents.

Non-limiting examples of crosslinking agents include a poly(ethylene glycol) diacrylate, a poly(ethylene glycol) dimethacrylate, diethylene glycol diacrylate, diethylene glycol dimethacrylate, ethylene glycol diacrylate, ethylene glycol dimethacrylate, N-(1-hydroxy-2,2-dimethoxyethyl)acrylamide, N,N'-(1,2-dihydroxyethylene)bisacrylamide, N,N'-methylenebisacrylamide (MBAAm), and any combination thereof.

The crosslinking level is determined by the amount of the crosslinking agent in the pre-polymerization mixture, relative to the number of monomers therein. Hence, the crosslinking level is defined by mol percent of the crosslinking agent in the total polymerizable units that constitute the polymer. According to some embodiments, the amount of the crosslinking agents in the pre-polymerization mixture ranges from a high of 100 mol percent (monomers are all capable of forming crosslinks as well as being part of the polymeric strand; for example, a system based on 100 mol % diacrylates and/or dimethacrylates) to a low of about 0.1 mol %, based on the total number of moles of polymerizable units (monomers and crosslinking agents), that constitute the pre-polymerization mixture. In some embodiments, the crosslinking level of the polymer in the composition-of-matter ranges from 5 to 20 mol percent, or alternatively is about 20 mol %, 19 mol %, 18 mol %, 17 mol %, 16 mol %, 15 mol %, 14 mol %, 13 mol %, 12 mol %, 11 mol %, 10 mol %, 9 mol %, 8 mol %, 7 mol %, 6 mol %, 5 mol %, 4 mol %, 3 mol %, 2 mol %, 1 mol %, 0.5 mol %, or 0.1 mol %.

Emulsion Stabilizers:

As discussed herein throughout, the matrix is a polyHIPE, which is the product of polymerization effected in the external phase of a HIPE, and thus the matrix is characterized by having a microstructure structurally-templated by the external phase of the HIPE, and the voids in the matrix are the residue of droplets of the internal phase of the HIPE. The biphasic structure of HIPEs can be maintained during polymerization under certain conditions, preferably using emulsion stabilizers, or HIPE-stabilizing agents.

HIPEs are inherently unstable and have a tendency to undergo phase inversion or phase coalescence. The HIPE structure, which is analogous to a conventional gas-liquid foam of low liquid content, gives rise to a number of properties including high viscosities and viscoelastic rheological behavior. Like dilute emulsions, HIPEs are intrinsically unstable; nevertheless, it is possible to prepare metastable systems which show no change in properties or appearance over long periods of time, or at least through a polymerization process of the external continuous phase.

Only a few of the available emulsion stabilizers (emulsifiers) are able to keep the major internal phase dispersed within the minor external phase. Some HIPE-stabilizing agents are insoluble in the internal phase and their molecular packing is capable of promoting the formation of a convex interface between the external and internal phases. As discussed hereinabove, one of the challenges in forming a polyHIPE is stabilizing the precursor HIPE though the polymerization reaction. In the context of embodiments of the present invention, suitable HIPE-stabilizing agents include surface-active substances (surfactants) and/or certain types of polymers and block copolymers (reactive and/or non-reactive; a polypeptide; a protein; an oligosaccharide; a polysaccharide), and/or solid surface-modified particles/nanoparticles (NP). In some embodiments, the effect of the abovementioned HIPE-stabilizing agents is further enhanced by salts.

According to some embodiments of the present invention, the emulsion stabilizer is a surfactant, which is present in the external phase of the precursor HIPE. Alternatively, in some embodiments, the surfactant is present in the internal and/or the external phase of the precursor HIPE. The surfactant is characterized, inter alia, by its hydrophilic-lipophilic balance (HLB). The hydrophilic-lipophilic balance of a surfactant is a measure of the degree to which it is hydrophilic or lipophilic, determined by calculating values for the different regions of the molecule. HLB values can be used to roughly predict the surfactant properties of a molecule, wherein HLB<10 is exhibited by a lipid-soluble (water-insoluble) surfactant, HLB>10 by water-soluble (lipid-insoluble) surfactant, 1 to 3 is an HLB of an anti-foaming agent, 3 to 8 is an HLB of a W/O (water in oil) emulsifier, 7 to 9 is an HLB of a wetting and spreading agent, 13 to 16 is an HLB of a detergent, 8 to 16 is an HLB of an O/W (oil in water) emulsifier, and 16 to 18 is an HLB of a solubilizer or hydrotrope. The surfactant used for stabilizing the precursor HIPE, en route to forming the composition-of-matter provided herein, is characterized, according to some embodiments of the present invention, by an HLB that ranges from 8 to 16.

Exemplary hydrophobic non-ionic surfactants include, without limitation, poloxamers, members of the alkylphenol hydroxypolyethylene family and a polyethoxylated sorbitan esters (polysorbitans). Other types of surfactants, such as anionic and cationic surfactants are also contemplated within the scope of the present invention. According to some embodiments of the present invention, the surfactant is nonionic surfactant.

In some embodiments, the surfactant is suitable for stabilizing oil-in-water HIPEs, such as members of the Tween family of surfactants, the Triton family of surfactants, sodium lauryl sulfate (SLS), sodium dodecyl sulfate (SDS), and, in addition block copolymers such as PEO-PPO-PEO and the likes.

In some embodiments, the surfactant is a member of the commercially available Pluronic® type surfactant, all of which are block copolymers based on poly(ethylene oxide) (PEO) and poly(propylene oxide) (PPO). Pluronics can function as antifoaming agents, wetting agents, dispersants, thickeners, and emulsifiers.

In some embodiments, the surfactant is an oil-soluble member of the commercially available Synperonic™ PE family of surfactants, constituting non-ionic, tri-block copolymer surfactants suitable for industrial and pharmaceutical applications. These poloxamers are chemically very similar, differing only in their poly(propylene oxide) to poly(ethylene oxide) content. This variation causes the physical and surface active properties of the poloxamers to vary.

In some embodiments, the surfactant is an oil-soluble member of the commercially available Kolliphor™ type surfactant.

According to some embodiments of the present invention, the HIPE is stabilized by a plurality of particles, or nanoparticles, forming a Pickering emulsion, as this term is known in the art. In the context of embodiments of the present invention, the nanoparticles are inorganic and/or organic nanoparticles which are suspendable in liquid media and can stabilize a HIPE, namely capable of forming Pickering HIPE compositions. As noted hereinabove, HIPEs can be stabilized with nanometer-sized particles to millimeter-sized particles, hence the description of surface modification of the particles applies to particles of all sizes.

The additional functionalities are added to the nanoparticles by surface modifications, affording modified particles or nanoparticles. The phrases "modified particles", "modified nanoparticles" and any particular examples thereof, such as "modified silica nanoparticles", refer to particles or nanoparticles which have been treated by one or more chemical reactions so as to modify the chemistry of their surface (surface-modified nanoparticles), thereby bestowing a chemical nature and/or a chemical reactivity to the nanoparticles which was not present in the parent nanoparticles. In general, when referring to inorganic and/or organic nanoparticles in the context an emulsion stabilizer of Pickering HIPE, according to embodiments of the present invention, it is meant to encompass a plurality of fully modified, partially modified and un-modified nanoparticles, unless one is specifically excluded.

The surface chemistry of the particles can be modified by any method or process known in the art, such as etching by acid, base, plasma or radiation. In the context of the present embodiments, a nanoparticle is modified by way of grafting, namely covalently attaching a plurality of chemical moieties thereto by reacting one or more surface-modifying agents with reactive surface groups which are found on the surface of the nanoparticle. The type of available reactive surface groups depends on the particular nanoparticle and the process of its manufacturing. Surface groups typically affect the interfacial tension of the nanoparticle in a given media. Typical reactive surface groups include, without limitation, hydroxyl groups, carbonyls, thiols, amines and the likes.

For instance, particles can be modified to present cross-linking moieties in addition to surface modifications for rendering the NP suitable HIPE-stabilizers; such modification makes the NP serve two roles, as HIPE-stabilizing agents and as crosslinking agent. For example, a polymerizable agent exhibiting a vinyl group can be grafted on the nanoparticle by reacting the same with reactive surface hydroxyl groups such that a plurality of polymerizable vinyl moieties is now covalently attached to its surface, thereby modifying the nanoparticle to act as a crosslinking agent as well as a HIPE-stabilizing agent. Similarly, a polymerization initiator agent (hereinafter "initiator" or "initiation agent") can be grafted onto the surface of the nanoparticle so as to modify the nanoparticle into an initiation agent due to a plurality of initiation moieties now found on its surface.

In some embodiments, the surfactant is suitable for stabilizing water-in-oil HIPEs, such as members of the Span family of surfactants (such as sorbitan monooleate (SMO), sorbitan monolaurate (SML)), polyglycerol polyricinoleate (PGPR), and the Hypermer family of surfactants. In some embodiments, the surfactant is selected from the group consisting of sorbitan monooleate, polyglycerol polyricinoleate, a hydrophobic-hydrophilic block copolymer, and any combination thereof. In some embodiments, the surfactant is Poloxamer 407, Triton X-405, Triton X-100, Triton X-705 and Tween 20. In the Examples section that follows, the poloxamer Pluronic® P-123, a $PEO_{20}$-$PPO_{70}$-$PEO_{20}$ triblock copolymer with poly(ethylene oxide) (PEO) and poly(propylene oxide) (PPO) blocks (Mn=5800), was used successful to stabilize the exemplary HIPE.

The concentration of the HIPE-stabilizing surfactant ranges, according to some embodiments of the present invention, from 0.01% to 30% by weight of the total weight of the external phase of the precursor HIPE. Alternatively, concentration of the HIPE-stabilizing surfactant ranges from 20% to 30% of the total weight of the external phase is usual for surfactants. It is noted herein that in case of Pickering emulsion stabilization, a very small amount of HIPE-stabilizing nanoparticles is sufficient to stabilize certain HIPEs, as low as 0.01 wt. % of total weight of the external phase.

Additional information regarding emulsion stabilizing solid particles can be found in the art [Silverstein, M. S., *Polymer*, 2014, 55, pp. 304-320; and Silverstein, M. S. and Cameron, N. R., *PolyHIPEs—Porous Polymers from High Internal Phase Emulsions*, Encyclopedia of Polymer Science and Technology, 2010].

Unique Properties:

Zwitterionic hydrogels have drawn much attention for their unique properties as responsive or "smart" polymers, an in particular their ability to swell and uptake an aqueous liquid in great amounts, relative to their dry mass. Additional information regarding polyzwitterionic hydrogels can be found in the literature, for example, in Gao, M. et al., "*Polyelectrolyte and antipolyelectrolyte effects in swelling of polyampholyte and polyzwitterionic charge balanced and charge offset hydrogels*", European Polymer Journal, 53, 2014, pp. 65-74, and in Wang, F., et al., "*Understanding anti-polyelectrolyte behavior of a well-defined polyzwitterion at the single-chain level*", Polym. Int., 2015, 64, pp. 999-1005.

The mechanical, chemical and physical properties, and to some extent, even the macroscopic structure, are influenced by the monomer composition of the polymer, particularly the electrostatic charge thereof. According to some embodiments of the present invention, the electrostatic charge of the hydrogel of the herein-disclosed composition-of-matter, together with the HIPE-templated microstructure thereof, endow unique properties thereto which are not exhibited by similar zwitterionic hydrogels not having a HIPE-templated microstructure, such as heightened anti-polyelectrolyte behavior, heightened dual pH-responsiveness, temperature responsiveness, heightened amounts of absorbate uptake, heightened rates of absorbate uptake, heightened sensitivity to the surrounding environment.

Being comprised of zwitterionic monomers, the HIPE-templated hydrogel presented herein can exhibit anti-polyelectrolyte behavior, as this term is known in the art, but the effect is heightened due to the HIPE-templated microstructure, and furthermore, the effect is strongly correlated to the degree of crosslinking in the hydrogel. As demonstrated in the Examples section that follows below (FIGS. 4A-E), when compared to a reference bulk (not HIPE-templated) hydrogel comprising identical polyzwitterionic composition, the HIPE-templated polyzwitterionic hydrogels presented herein exhibit increased salt solution uptakes. The amplification of the anti-polyelectrolyte effect may be explained by hydrogel-swelling-driven void expansion, which is often the dominant factor in the uptake within HG-PHs. Without being bound by any particular theory, it is assumed that the ability to swell and absorb aqueous absorbate, which is common to both the composition-of-matter presented herein and a corresponding reference bulk polymer, is overshadowed many folds by hydrogel-swelling-driven void expansion that produces a multi-fold increase in void size. If the composition-of-matter presented herein was acting merely as a sponge, the voids would be filled with the absorbate, however, the unique combination of the HIPE-templated microstructure and the polyzwitterionic composition, allows the composition-of-matter presented herein to absorb aqueous medium at a rate much greater than that of the reference bulk HG.

According to some embodiments, the composition-of-matter presented herein is an anti-polyelectrolyte, since the uptake of a solution of an ionic solute at a first concentration is higher than the uptake on a solution at a second concentration, wherein the first concentration is higher than the second concentration.

The composition-of-matter presented herein also exhibits dual pH-responsiveness; a dual pH-response is expressed by an increase in solution uptake when the solution's pH is either greater or smaller than the pH at the isoelectric point of the Z-HG-PH. This dual pH-responsiveness is much more pronounced when compared to that exhibited by a reference bulk HG of identical polymeric composition.

The net charge on the molecule is affected by pH of its surrounding environment and can become more positively or negatively charged due to the gain or loss, respectively, of protons (H+). The isoelectric point (IEP; pH(I); pI) of the composition-of-matter is defined as the pH at which composition-of-matter carries a neutral (zero) net electrical charge in the statistical sense.

The pH-responsive uptake mechanism, similar to the NaCl solution uptake mechanism, can be understood through osmotic pressure effects. Since a composition-of-matter can be designed to be electrostatically neutral at a neutral pH (IEP=7), the absorbate uptake is driven by the relatively small osmotic pressure generated during swelling, and that is presumably the reason that the Z-HG-PHs exhibit relatively low uptakes at a neutral pH. However, at low or high pH, mobile ions ($H^+$ or $OH^-$) are introduced, and their presence increases the osmotic pressure, which is the force behind the observed increase in absorbate uptake with pH.

Figures 5A, 5B, 5C:
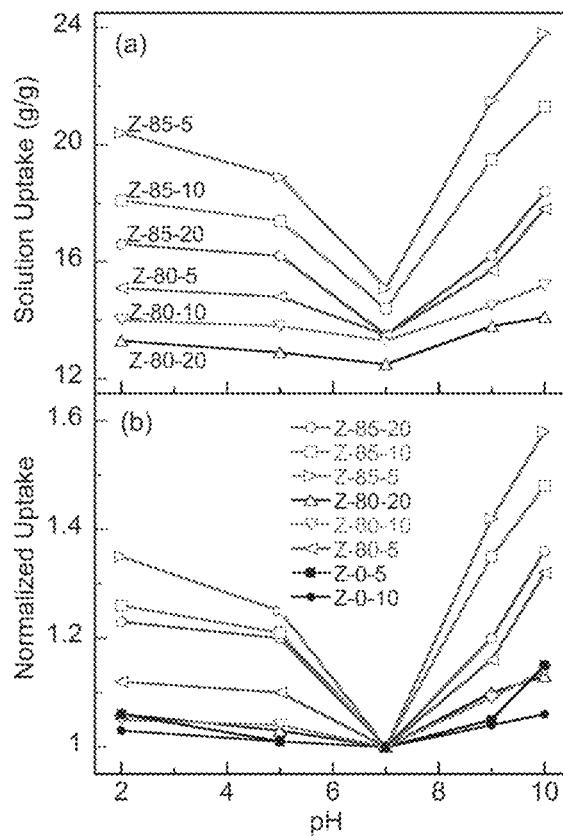
FIGS. 5A-C present comparative plots showing the effects of solution pH on the solution uptake on various HG samples (FIG. 5A), the effects of solution pH normalized by the uptake at pH 7 (FIG. 5B), and the uptake of water at pH 2 within the water-swollen Z-X-5 samples (FIG. 5C)

According to some embodiments, the composition-of-matter presented herein is characterized by a pH-responsive solution uptake, wherein an uptake of a solution having a pH below or above the isoelectric point of the composition-of-matter, is higher than the uptake at said isoelectric point, and increases proportionally to the difference between the surrounding pH and the IEP. This effect is demonstrated, for example, by the results presented in FIGS. 5A-B, presented in the Examples section that follows below.

The Z-HG-PH presented herein surprisingly exhibit a notable temperature-responsiveness, as demonstrated in the Examples section below (FIGS. 6A-D). A temperature increase from 5 to 60° C. produced an increase in absorbate uptake, reflecting an increase in the mobility of the zwitterionic pendant groups, and an increase in the dissociation constant of water, both of which contribute to an increase in the osmotic pressure, leading to increase uptake. This temperature-responsiveness is not observed in chemically corresponding non-HIPE-templated reference bulk HGs.

According to some embodiments, the composition-of-matter presented herein is characterized by a temperature-responsive solution uptake, wherein an uptake of a solution at a first temperature is higher than the uptake of a solution at a second temperature, wherein the first temperature is lower than the second temperature.

Imbalanced Charge Stoichiometric Ratio:

As stated hereinabove, the polymer can be a homopolymer with 100% of one type of zwitterionic monomers, or a copolymer with more than one type of zwitterionic monomers but 100% zwitterionic monomers, or it can be a copolymer made with zwitterionic monomers and other monomers, such as non-ionic monomers, negatively charged monomers and/or positively charged monomers. It is noted that when referring to the chemical nature of a monomer, it is meant that the side-chain, or pendant group is the bearer of the functionality; thus, for example, a positively charged monomer is a monomer that imparts a positively charged pendant group to the polymer of which it forms a part.

According to some embodiments of the present invention, non-ionic monomers are incorporated into the polymer of the composition-of-matter presented herein; these monomers can endow various properties to the resulting composition-of-matter, such as elasticity, and can be used to fine-tune/attenuate charge-related properties that are conferred by the zwitterionic monomers. Exemplary non-ionic monomers include, without limitation, hydroxy alkyl celluloses, poly(ethylene glycol) acrylates, poly(ethylene glycol) methacrylates, polyoxazolidones, polyvinyl methyl ethers, N,N-dialkylacrylamides, 2-hydroxyethyl acrylate, 2-hydroxyethyl methacrylate, acrylamide, diacetone acrylamide, dimethylaminoethyl methacrylate (DMAEMA), glycidyl methacrylate, N-(1-hydroxy-2,2-dimethoxyethyl)acrylamide, N,N-dimethylacrylamide, N-[3-(dimethylamino)propyl]methacrylamide, N-acryloylpyrrolidine, N-alkylacrylamide, N-hydroxyethyl acrylamide, N-isopropyl acrylamide, N-vinylimidazoline, polyethlyene oxide, polymethacrylic acid, styrene, vinyl acetate, and their water-soluble non-ionic derivatives.

According to some embodiments of the present invention, monomers bearing positively charged pendant groups are incorporated into the polymer of the composition-of-matter presented herein; these monomers add cationic charge to the polymer, and can be used to fine-tune charge-dependent properties that are conferred by the zwitterionic monomers. Exemplary positively charged monomers (monomers having said positively charged pendant group) include, without limitation, (3-acrylamidopropyl)trimethylammonium chloride, (vinylbenzyl)trimethylammonium chloride, [2-(methacryloyloxy)ethyl]trimethylammonium chloride, [3-(methacryloylamino)propyl]trimethylammonium chloride, 1-vinyl-5-aminotetrazole, 2-(dimethylamino)ethyl acrylate, 2-(dimethylamino)ethyl methacrylate, 2-[3-(6-methyl-4-oxo-1,4-dihydropyrimidin-2-yl)ureido]ethyl methacrylate, 2-methacryloxyethyltrimethylammonium chloride, 3-methacryloxy-2-hydroxypropyltrimethylammonium chloride, diallyldimethylammonium chloride, 2-acryloxyethyltrimethylammonium chloride, and their salts and positively charged derivatives.

According to some embodiments of the present invention, monomers bearing negatively charged pendant groups are incorporated into the polymer of the composition-of-matter presented herein; these monomers add anionic charge to the polymer, and can be used to fine-tune charge-dependent properties that are conferred by the zwitterionic monomers. Exemplary negatively charged monomers (monomers having said negatively charged pendant group) include, without limitation, acrylic acid, methacrylic acid, 2-acrylamido-2-methyl-1-propanesulfonic acid (PAMPS; AMPSA), 2-carboxyethylacrylate, 2-methyl-2-propene-1-sulfonic acid, 2-propene-1-sulfonic acid, 2-sulfoethyl methacrylate, 3-butene-1,2,3-tricarboxylic acid, 3-sulfopropyl methacrylate, 4,4-Bis(4-hydroxyphenyl)pentanoic acid, 4-styrenesulfonic acid, 4-vinylbenzoic acid, bis(2-methacryloxyethyl)phosphate, bisacrylamidoacetic acid, itaconic acid, monoacryloxyethyl phosphate, styrene sulfonate (4-vinylbenzenesulfonate), vinylsulfonic acid, and their salts and negatively charged derivatives.

In general, a Z-HG-PH based solely on zwitterionic monomers is said to have a balanced charge or a charge stoichiometric ratio of 1, namely the IEP thereof is essentially neutral. This parameter can be fine-tuned and offset by introducing non-ionic monomers, and/or charge-bearing monomers, into the pre-polymerization mixture (the external phase of the HIPE). Copolymers such as these afford Z-HG-PHs with different charge stoichiometric ratios. Without being bound by any particular theory, it is assumed that charge imbalance in the Z-HG-PH may shift the isoelectric point, and thus affect the above-described properties accordingly. For example, it assumed feasible to fine-tune the charge of the Z-HG-PH so as to offset to anionic by including negatively charged pendant groups to the hydrogel, thereby shifting the dual pH-responsiveness towards increased uptake of more acidic solutions (IEP shift to a lower pH value), and vice versa. For additional information regarding augmenting and fine-tuning the charge-related properties of hydrogels see, for example, Tan, B. H. et al., "*Synthesis and aqueous solution properties of sterically stabilized pH-responsive polyampholyte microgels*", Journal of Colloid and Interface Science, 2007, 309(2), pp 453-463, and Maji, T. et al., "*Dual-Stimuli-Responsive l-Serine-Based Zwitterionic UCST-Type Polymer with Tunable Thermosensitivity*", Macromolecules, 2015, 48(14), pp 4957-4966.

Process of Preparation:

While reducing the present invention to practice, it was found that the preparation of a polyzwitterionic polyHIPE is not trivial, possibly due to the inner electrostatic forces acting therein. In particular, removal of the internal organic phase after polymerization was found to be challenging, and an exchange of the water-immiscible organic solvent with a more water-miscible solvent had to be added to the process.

According to an aspect of some embodiments of the present invention, there is provided a process of preparing the composition-of-matter presented herein, the process includes preparing and subjecting a high internal phase emulsion (HIPE) having an internal phase and a polymerizable external phase to polymerization of the polymerizable external phase, which includes a plurality of zwitterionic monomers and at least one crosslinking agent.

In some embodiments, the internal phase is a water-immiscible organic solvent, and the polymerizable internal phase in an aqueous pre-polymerization mixture of monomers. The phases are mixed thoroughly so as to achieve an oil-in-water HIPE. In some embodiments, a thickening agent is used in any one of the phases in order to bring its viscosity closer to the viscosity of the other phase.

The HIPE is prepared at a temperature at which the phases are both in a liquid state. In some embodiments, the temperature at which the HIPE is prepared ranges from 0° C. to 100° C., or 25-80° C., or 35-80° C., depending on the contents of the phases. For instance, if the one phase includes a room-temperature solid, the HIPE is prepared at the temperature at which the solid melts to a mixable liquid or higher, but lower than its boiling point, and lower than the boiling point of the other phase. In some embodiments wherein polymerization is effected by increasing the temperature of the HIPE, the HIPE is prepared at a temperature lower than the activation temperature of the polymerization initiator, and once afforded, the temperature is raised to the activation temperature so as to effect polymerization of the external phase of the HIPE.

Once the HIPE is prepared, the polymerization reaction is initiated in a manner appropriate for the specific polymerization reaction and the polymerization initiating agent (initiator). In some embodiments, the initiator is added to one of the HIPE phases, and when the HIPE is ready, the external stimulus is activated, such as heat, irradiation and the likes. In some embodiments, the initiator is added to the ready HIPE just before mixing is halted to allow the structure to form.

As discussed hereinabove, once the polymerization reacting is complete, and the polyHIPE is fully formed, the internal phase is removed from the polyHIPE by means of vacuum, extraction or drying. In some embodiments, the internal phase is removed in several steps that include exchanging the water-immiscible organic solvent or melt with a water-miscible organic solvent. Exchanging the water-immiscible solvent can be effected by Soxhlet extraction or immersion in the water-miscible organic solvent. In some embodiments, the solvent exchange is effected at a relative low temperature, e.g., at a temperature lower than 0° C.

Exemplary water-miscible organic solvent that can be used to replace the water-immiscible solvent include, without limitation, an alcohol such as methanol, ethanol, propanol and isopropanol, as well as acetone, acetonitrile, N,N-dimethylformamide (DMF) and dimethylsulfoxide (DMSO).

Once the internal phase has been replaced, removal of the water-miscible organic solvent is effected extraction and/or washes, and the remaining solvent is removed by heat, vacuum, freeze-drying and/or ambient drying.

Article-of-Manufacturing:

According to yet another aspect of the present invention, there is provided an article-of-manufacturing which includes, or is based on the HIPE-templated zwitterionic hydrogels, or composition-of-matter, as presented herein.

The composition-of-matter presented herein is designed to absorb and contain, in the form of a hydrogel, any type of an aqueous solution, even under considerable compressive strain. The zwitterionic nature of the pendant groups allows deionized water, and even more so water containing any solutes (salts and other water-soluble chemical entities), to be absorbed in the composition-of-matter. As demonstrated in the Examples section below, the composition-of-matter presented herein, according to some embodiments of the present invention, were shown to be highly effective in absorbing, at considerable mass ratios, water at any pH, particularly non-neutral pH, salt solutions and urine.

Thus, the composition-of-matter can serve as an excellent liquid absorbing and/or retaining hydrogel substance and matrix for a variety of uses.

According to an aspect of some embodiments of the present invention, the composition-of-matter forms a part or is an article of manufacturing, either in the dry or the wet form as partially hydrated, partially swollen or fully swollen hydrogels.

Due to their unique mechanical properties, the composition-of-matter can be cast in the liquid HIPE form into any shape and size mold before polymerization, or they can be reshaped and further processed post casting and polymerization in the dry or wet form. The composition-of-matter can therefore take any size of a block, a sphere, a rod, a particle (powder), a flat or shaped sheet or membrane, a tube or a fiber.

The article of manufacturing in which the composition-of-matter is incorporated can be any one of the non-limiting examples that include a basic solution retention device, an acidic solution retention device, a cosmetic product, a diaper, a filter material, matrix or device, a flood/spill control material or device, a grooming product, a liquid waste material or device, a personal care and/or hygiene product, a surgical pad, a water purification material, matrix or device, a water retention material or containing device, a wound dressing, an incontinence garment, and an ion-exchange material, matrix or device.

It is expected that during the life of a patent maturing from this application many relevant HIPE-templated zwitterionic hydrogels will be developed and the scope of the term "HIPE-templated zwitterionic hydrogels" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the phrases "substantially devoid of" and/or "essentially devoid of" in the context of a certain substance, refer to a composition that is totally devoid of this substance or includes less than about 5, 1, 0.5 or 0.1 percent of the substance by total weight or volume of the composition. Alternatively, the phrases "substantially devoid of" and/or "essentially devoid of" in the context of a process, a method, a property or a characteristic, refer to a process, a composition, a structure or an article that is totally devoid of a certain process/method step, or a certain property or a certain characteristic, or a process/method wherein the certain process/method step is effected at less than about 5, 1, 0.5 or 0.1 percent compared to a given standard process/method, or property or a characteristic characterized by less than about 5, 1, 0.5 or 0.1 percent of the property or characteristic, compared to a given standard.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions; illustrate the invention in a non-limiting fashion.

Example 1

Materials and Methods

Highly porous zwitterionic hydrogel polyHIPEs (Z-HG-PHs) were synthesized within oil-in-water high internal phase emulsions (HIPEs) (N-(3-sulfopropyl)-N-(methacryloxyethyl)-N,N-dimethylammonium betaine (SBMA) cross-linked with N,N'-methylenebisacrylamide) (MBAAm).

Materials:

SBMA, Pluronic® P-123 (a $PEO_{20}$-$PPO_{70}$-$PEO_{20}$ triblock copolymer with poly(ethylene oxide) (PEO) and poly(propylene oxide) (PPO) blocks, Mn=5800), MBAAm, N,N,N',N'-tetramethylethylenediamine (TEMED), acrylamide (AAm) and sodium acrylate (NaA) were from Sigma-Aldrich, while ammonium persulfate (APS) was from Fluka. All the chemicals were used as received. The other reagents such as ethanol (EMSURE®) and NaCl (Bio-lab Ltd.) were analytical grade. Deionized water was used for all the experiments.

Artificial urine was prepared using a recipe in the literature; briefly: 36.4 g urea, 15.0 g NaCl, 9.0 g KCl and 9.6 g $Na_3PO_4$ were dissolved in 1.5 L deionized water. The pH of the aqueous solution was then adjusted to 6 using a 0.1 M NaOH solution.

Synthesis:

P-123, SBMA, MBAAm and APS were dissolved in deionized water and stirred with an overhead stirrer at 400 rpm. Hexane was added dropwise to the aqueous solution under stirring, which was continued for another 3 minutes following the addition of hexane to enhance HIPE homogeneity. The stirring speed was then reduced to 50 rpm and the TEMED was added. The HIPE polymerization was conducted for 10 hours in a convection oven at 40° C. The as-synthesized polyHIPEs were transferred to a freezer (−25° C.) for 2 hours before being cut into cubes for solvent exchange. Solvent exchange with ethanol was carried out at −25° C., by immersing the 1 $cm^3$ cubes in 3 mL of ethanol for 24 hours. Unreacted monomers were then removed through Soxhlet extraction in ethanol for 24 hours. The resulting Z-HG-PHs were then dried in a vacuum oven at room temperature for 24 hours.

The recipes for the SBMA-containing Z-HG-PHs are listed in Table 1, and denoted Z-X-Y wherein X represents the mass fraction of the dispersed phase in the HIPE and Y represents the mole fraction of MBAAm in the monomers, namely the crosslinking level.

TABLE 1

|  | Z-85-20 | Z-85-10 | Z-85-5 | Z-80-20 | Z-80-10 | Z-80-5 | Z-75-20 |
|---|---|---|---|---|---|---|---|
| Aqueous, continuous phase (wt %) | | | | | | | |
| Water | 9.32 | 9.64 | 9.77 | 12.29 | 12.69 | 12.87 | 16.21 |
| P-123 | 0.77 | 0.77 | 0.77 | 1.01 | 1.01 | 1.01 | 1.34 |
| SBMA | 4.10 | 4.10 | 4.10 | 5.40 | 5.40 | 5.40 | 7.13 |
| MBAAm | 0.57 | 0.25 | 0.12 | 0.74 | 0.34 | 0.16 | 0.98 |
| APS | 0.10 | 0.10 | 0.10 | 0.13 | 0.13 | 0.13 | 0.18 |
| Total | 14.86 | 14.86 | 14.86 | 19.57 | 19.57 | 19.57 | 25.84 |
| Organic, dispersed phase (wt %) | | | | | | | |
| Hexane | 85.04 | 85.04 | 85.04 | 80.30 | 80.30 | 80.30 | 73.98 |
| Catalyst added following HIPE formation (wt %) | | | | | | | |
| TEMED | 0.10 | 0.10 | 0.10 | 0.13 | 0.13 | 0.13 | 0.18 |

Reference bulk zwitterionic hydrogels (not HIPE-templated) were also prepared and termed Z-0-Y, where 0 indicates that there is no internal phase and Y represents the mole fraction of MBAAm in the monomers. The Z-0-Y reference zwitterionic hydrogels were prepared using the same recipes as those for the continuous phases of the corresponding Z-X-Y (but without the surfactant P-123) and the polymerizations were carried out under the same conditions as those for the Z-X-Y. The resultant Z-0-Y were swollen in water for one week to remove the residual monomers (the Z-0-Y: water mass ratio was larger than 1:20 and the water was changed every day).

The PH-80-10-V reference HG-PHs were prepared using the same procedures used to synthesize the Z-X-Y (Table 2), wherein "80" represents the mass fraction of the dispersed phase, "10" represents the mole fraction of MBAAm in the monomers, and V represents the mole fraction of NaA in the monomers.

TABLE 2

|  | PH-80-10-30 | PH-80-10-0 |
|---|---|---|
| Aqueous, continuous phase (wt %) | | |
| Water | 12.38 | 13.00 |
| P-123 | 1.17 | 1.17 |
| AAm | 3.24 | 4.86 |
| NaA | 2.13 | 0 |
| MBAAm | 1.16 | 1.16 |
| APS | 0.12 | 0.12 |
| Total | 20.20 | 20.19 |

TABLE 2-continued

|  | PH-80-10-30 | PH-80-10-0 |
|---|---|---|
| Organic, dispersed phase (wt %) | | |
| Hexane | 79.71 | 79.72 |
| Catalyst added following HIPE formation (wt %) | | |
| TEMED | 0.09 | 0.09 |

Synthesis Results and Characterization:

The as-synthesized Z-HG-PHs (X: 75, 80, 85 wt %; Y: 5, 10, 20 mol %). The Z-X-Y, with average polymerization yields of around 84%, were white monoliths, as expected for a material with micrometer-scale voids. Table 3 presents yield, density, and macroporous structure of the Z-HG-PHs.

The polymerization yields were obtained from a mass balance following the Soxhlet extraction, and the density was calculated gravimetrically. The chemical compositions were investigated using FUR spectroscopy (Bruker Equinox 55FTIR spectrometer) in transmission. The polymers were ground with KBr and pressed into pellets. The spectra were recorded using an average of 64 scans, the wavenumbers ranged between 600 and 4000 $cm^{-1}$, and the resolution was 4 $cm^{-1}$. The porous structures of the polyHIPEs were described using SEM (FEI Quanta 200) at 20 kV. The cryogenic fracture surfaces were coated with a thin gold-palladium layer. The average void and interconnecting wall-hole diameters were calculated by measuring 100 voids and 100 interconnecting holes in the SEM micrographs at low magnification. The average void diameter was corrected for the random nature of the section by multiplying by $2/(3^{1/2})$.

TABLE 3

|  | Z-85-20 | Z-85-10 | Z-85-5 | Z-80-20 | Z-80-10 | Z-80-5 | Z-75-20 |
|---|---|---|---|---|---|---|---|
| $Y_p$ (%) | 85 | 85 | 82 | 84 | 85 | 83 | 88 |
| $\rho_{PH}$ (g $cm^{-3}$) | 0.124 | 0.124 | 0.164 | 0.158 | 0.160 | 0.189 | 0.161 |
| $d_v$ (μm) | 24.7 | 34.0 | 24.0 | 22.9 | 23.7 | 29.6 | 52.1 |
| $d_w$ (μm) | 3.1 | 5.2 | 3.4 | 4.1 | 3.6 | 4.5 | 6.0 |

The presence of SBMA and the increase in the MBAAm content with Y were confirmed for the Z-80-Y using Fourier transform infrared spectroscopy (FTIR).

The density of the Z-X-Y samples varied from 0.124 g cm$^{-3}$ for Z-85-20 to 0.189 g cm$^{-3}$ for Z-80-5. As expected, the densities of the Z-X-Y samples increased with the reduction in the dispersed phase content. The density also increased with the reduction in the MBAAm content, indicating that the crosslinking limits the extent of shrinkage during polymerization and drying.

PSBMA in water is known to exhibit an upper critical solution temperature (UCST) at 32-37° C. and undergo phase separation. If such phase separation occurs during hydrogel synthesis, it would have a negative impact on the resulting network structure. Crosslinking PSBMA with MBAAm, however, has been observed to suppress the physical interactions between the zwitterionic groups that lead to phase separation. The Z-0-Y reference hydrogels, synthesized at temperatures ranging 0-60° C., were all transparent with no visible heterogeneities, indicating that extensive phase separation did not occur during synthesis.

The influence of the Z-80-Y monomer composition on the macromolecular structure was investigated using Fourier transform infrared spectroscopy (FTIR), and the FTIR spectra, presented in FIG. 1, were normalized by the peak height at 1190 cm$^{-1}$ that is associated with the carbonyl group in SBMA.

FIG. 1 presents an FTIR spectra of the Z-80-Y sample, normalized using the peak height at 1190 cm$^{-1}$.

As can be seen in FIG. 1, for SBMA the peaks at 737 and 1043 cm$^{-1}$ are the characteristic absorptions for —C—S— and —S=O, respectively, and the peak at 1731 cm$^{-1}$ is the characteristic absorption of the carboxyl group. For MBAAm the absorption peaks at 1644 and 1538 cm$^{-1}$ are associate with the amide I C=O stretch and the amide II —N—H vibration, respectively. These latter assignments were confirmed by the decrease in the normalized peak heights at 1644 and 1538 cm$^{-1}$ with the decrease in the Z-80-Y MBAAm content.

The porous structures of the dried Z-X-Y were characterized using scanning electron microscopy (SEM).

FIGS. 2A-F present the porous structures of the Z-80-Y and Z-85-Y as seen in SEM micrographs, wherein FIG. 2A shows the Z-80-20 sample, FIG. 2B shows the Z-80-10 sample, FIG. 2C shows the Z-80-5 sample, FIG. 2D shows the Z-85-20 sample, FIG. 2E shows the Z-85-10 sample, and FIG. 2F shows the Z-85-5 sample.

As can be seen in FIGS. 2A-F, all the Z-X-Y samples possessed interconnected macroporous structures, exhibiting an average void diameter ranging from 22.9 to 52.1 µm and the average interconnecting hole diameters ranging from 3.1 to 6.0 µm (see, Table 3), with the void diameter distribution data, including Gaussian curve fits (see, FIGS. 3A-G).

Figure 3G:
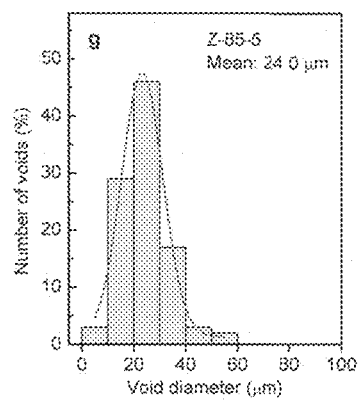

FIGS. 3A-G show the void diameter distribution in sample Z-75-20 (FIG. 3A), sample Z-80-20 (FIG. 3B), sample Z-80-10 (FIG. 3C), sample Z-80-5 (FIG. 3D), sample Z-85-20 (FIG. 3E), sample Z-85-10 (FIG. 3F), and sample Z-85-5 (FIG. 3G).

The Z-X-Y porous morphologies are similar to those of typical, surfactant-stabilized polyHIPEs. The highly interconnected, micrometer-scale porous structures are expected to facilitate the rapid absorption of aqueous solutions through capillary action.

Liquid Uptake Determination:

The liquid uptake of the Z-X-Y samples was evaluated both in the dry (dehydrated) state and in the liquid-swollen (hydrated) state. Dehydrated Z-X-Y samples were placed in a variety of solutions (different NaCl concentrations, different pH values, water at different temperatures, artificial urine, or 6 M HCl solution) to obtain the absolute hydrated form thereof. The liquid uptake by liquid-swollen hydrogel were used to compare the response rates of the Z-X-Y samples and the Z-0-Y reference samples (the Z-0-Y broke into small pieces during drying, and therefore, the uptakes of dry samples could not be evaluated). In this scenario, liquid-swollen Z-X-Y and Z-0-Y samples were immersed in a 0.75 M NaCl solution, in water at pH 2, or in water at pH 10, and the liquid uptake was followed as a function of time.

The equilibrium water/solution/liquid uptake was determined by the change in mass. Typically, a sample cube (about 1 cm×1 cm×1 cm) with a known dry mass ($m_d$) was placed in an aqueous solution until a swollen equilibrium mass ($m_{sw,i}$) was reached (i represents the absorbate identity (for example, "0.75" for an NaCl concentration of 0.75 M, "W" for water at pH 7, "2" for water at pH 2, or "10" for water at pH 10). The uptake ($U_i$) was calculated using Equation 1 (an average of at least three samples), $$U_i = (m_{sw,i} - m_d)/m_d \qquad \text{Equation 1}$$

The liquid uptake was determined in this manner for water at various pHs, water at various temperatures, NaCl solutions, urine, and a 6 M HCl solution. NaCl was chosen as the model electrolyte since it is commonly found in aqueous solutions (urine, saline solutions). The NaCl concentrations were varied from 0 to 0.75 M in 0.15 M increments. The mass ratio of the aqueous solution to the final, water-swollen sample was over 100:1 such that changes in the salt solution concentration during the experiment were minimized.

The normalized uptake ($U_N$) in the 0.75 M solution is the ratio of the equilibrium liquid uptake of the 0.75 M NaCl solution ($U_{0.75}$) to the equilibrium uptake of water ($U_W$) as shown in Equation 2. The water-swollen Z-X-5 and Z-0-5 were used to study the response to changes in NaCl concentration or in pH. The water-swollen cubes of Z-X-5 and Z-0-5 were placed in 150 mL of a 0.75 M NaCl solution, water at pH 10, or water at pH 2. The fraction of the increase in the equilibrium uptake ($U_{j,f}$) from the original water uptake ($m_{sw,W}$) was calculated using Equation 3 where j represents the nature of the second absorbate, whereas water was the first absorbate.

$$U_N = U_{0.75}/U_W; \qquad \text{Equation 2}$$

$$U_{j,f} = (m_{t,j} - m_{sw,W})/(m_{sw,j} - m_{sw,W}); \qquad \text{Equation 3}$$

where $m_{t,j}$ denotes the mass of the hydrogel after a time t in the second absorbate represented by j (for example, "0.75" for an NaCl concentration of 0.75 M, "W" for water at pH 7, "2" for water at pH 2, or "10" for water at pH 10).

Aqueous solutions with pHs of 2, 5, 7, 9 or 10 were obtained using either HCl or NaOH (the pH was verified using indicator paper). Buffers were not used to establish the pH since they could affect the results by having an electrolyte effect. Relatively large solution to water-swollen polymer mass ratios, larger than 100:1, were used such that changes in the solution pH with time were minimized. No changes in pH were observed during the experiments. The liquid uptake of the samples was calculated using Equation 1 and the normalized liquid uptake was calculated using Equation 2. The response rates were investigated by following the absorption of pH 2 and pH 10 solutions by the water-swollen polymers using Equation 3.

Example 2

HIPE-Templated Zwitterionic Hydrogel Properties

The Z-HG-PH samples, obtained as described hereinabove, exhibited anti-electrolyte behavior, responsive uptakes (dual-pH/temperature), concentrated acid uptake and storage, and relatively large urine uptakes. Emulsion templating amplified the anti-polyelectrolyte effect and the sensitivities, rates, and magnitudes of the responsive uptakes.

Anti-Polyelectrolyte Effect and Amplified Response:

The usual salt-solution-uptake behavior observed for HG-PHs, decreasing uptake with increasing salt concentration, is termed the polyelectrolyte effect. The increase in uptake with increasing salt concentration, as demonstrated here for the Z-HG-PHs, has been termed the anti-polyelectrolyte effect. The water uptake of the Z-X-20 was found to be tunable through the content of the dispersed phase, by increasing from 8.2 g g$^{-1}$ for Z-75-20 (lower internal phase content) to 13.3 g g$^{-1}$ for Z-85-20 (higher internal phase content).

FIGS. 4A-E present comparative plots of NaCl solution uptake as a function of NaCl concentration by various samples: Z-X-20 (FIG. 4A), Z-85-Y (FIG. 4B), and the effect of the MBAAm content on the uptake: uptake of a 0.75 M NaCl solution normalized by the uptake of water (FIG. 4C), uptake of water and artificial urine (FIG. 4D), and uptake of NaCl solutions by Z-80-Y (FIG. 4E).

As can be seen in FIGS. 4A-E, the uptake is salt-concentration-responsive (FIG. 4A), whereas the uptake increases with increasing NaCl concentration (from 0 to 0.75 M). Thus, the uptake behavior of Z-HG-PHs is very different from the behavior of conventional HG-PHs. The anti-polyelectrolyte effect, which was observed for all the Z-85-Y and Z-80-Y, would be highly advantageous for absorption applications involving relatively highly concentrated salt solutions since the absorbent effectiveness increases with increasing salt concentration. As can further be seen in FIGS. 4A-D, reducing the crosslinking comonomer content from 20 to 5 mol % produced a slight increase in water uptake, from 13.3 to 15.0 g g$^{-1}$, in the Z-85-Y (FIG. 4B) and a similar increase in the Z-80-Y (FIG. 4E). This increase in uptake reflects the increase in macromolecular mobility associated with the decrease in crosslinking.

The influence of the crosslinking comonomer content and the internal phase content on the anti-polyelectrolyte effect can be understood more clearly by normalizing the uptake of a 0.75 M NaCl solution by the uptake of water. The normalized uptakes in samples Z-85-Y and Z-80-Y decreased significantly with increasing crosslinking comonomer content (FIG. 4C) and with decreasing internal phase content. In addition, the normalized uptakes in the Z-X-Y samples are significantly higher than those in the corresponding reference hydrogels (FIG. 4C). The response of the zwitterionic hydrogels to immersion in an aqueous solution was amplified through the generation of a highly porous structure through emulsion templating. This amplification of the anti-polyelectrolyte effect in the Z-X-Y samples originates in the hydrogel-swelling-driven void expansion, which is often the dominant factor in the uptake within HG-PHs.

Solution-swollen, salt-sensitive hydrogels usually consist of three components: a three-dimensional network, an ionic species, and an absorbed solution. The shrinkage and swelling of these hydrogels depend on the ionic interactions between the fixed charges on the polymer and the mobile ions in the solution. These interactions contribute significantly to the osmotic pressure between the swollen hydrogel and the external solution; in the Z-X-Y samples there are both positive and negative charges fixed on the polymer. Water-swollen hydrogels contain negligible amounts of mobile ions (trace ions only). An osmotic pressure develops from the concentration difference that is generated upon immersion of the water-swollen hydrogel in NaCl solution. This osmotic pressure then drives the hydrogel's absorption of the solution. In the Z-HG-PHs, the consequent increase in absorption produces an increase in the hydrogel-swelling-driven void expansion, and thus, an increase in the overall uptake.

The anti-polyelectrolyte effect behavior indicates that Z-HG-PHs might have properties of interest for the absorption of bodily fluids. As a proof-of-concept, the Z-X-Y urine uptake was investigated. Surprisingly, and highly unusually, the solution uptake was significantly higher than that of water (FIG. 4D). Similar to the trends seen for the uptake of NaCl solutions in FIG. 4C, the urine uptake increased significantly with increasing porosity (internal phase content) and with decreasing macromolecular mobility (crosslinking comonomer content).

Dual-pH Response:

Hydrogels possessing ionizable groups are usually pH-responsive. The uptake is affected by the interaction of the HG's ionic groups with H$^+$ at low pH or with OH$^-$ at high pH. Conventional HG-PHs have either fixed positive groups or fixed negative groups, and therefore, their solution uptake is responsive to either H$^+$ or OH$^-$ concentration, but not to both, and as a result, the uptakes by such HG-PHs usually vary monotonically with the pH. The Z-X-Y sample, however, possess both fixed positive groups and fixed negative groups. These polymers, therefore, were found to exhibit a dual pH-responsive uptake since interactions with both H$^+$ and OH$^-$ are possible.

The water uptake by the Z-X-Y samples were studied in a relatively mild pH range, between 2 and 10, to minimize decomposition effects, and the results are presented in FIGS. 5A-C.

FIGS. 5A-C present comparative plots showing the effect of solution pH on the solution uptake on various HG samples (FIG. 5A), normalized by the uptake at pH 7 (FIG. 5B, and the uptake of water at pH 2 within the water-swollen Z-X-5 sample (FIG. 5C).

As can be seen in FIGS. 5A-C, the water uptake of the Z-80-Y and the Z-85-Y (FIG. 5A), which are strongly pH-dependent, exhibit a dual pH-responsive behavior. The uptake decreased from pH 2 to 7 and then increased from pH 7 to 10. Overall, the lowest uptake was at pH 7 and the highest uptake was at pH 10. The effects of the crosslinking comonomer content and of the internal phase content on the water uptake were studied by comparing the pH dependence of the uptakes of the Z-X-Y and the Z-0-Y, normalizing the results by the uptake at pH 7 (FIG. 5B); the normalized uptakes demonstrate that the Z-X-Y are significantly more response-sensitive to the pH than the corresponding Z-0-Y. Here, too, HIPE-templating of the Z-HG-PHs amplified the pH response seen in the Z-0-Y. The increase in water uptake in the Z-X-Y, at low or high pH, may be partially driven by the increase in the concentration of the pH-determining electrolyte (0.01 M HCl or 0.001 M NaOH). However, these low concentrations of electrolyte are not expected to have a significant effect on the Z-X-Y uptake, as other electrolytes, such as NaCl, did not produce significant increases in uptake at such low concentrations.

The pH-responsive uptake mechanism, similar to the NaCl solution uptake mechanism, can be understood through osmotic pressure effects. Since SBMA is electrostatically neutral, the uptake in the Z-X-Y samples is driven by the relatively small osmotic pressure generated during absorption. For this reason, the Z-X-Y samples exhibit relatively low uptakes at a neutral pH. However, at low pH ($H^+$) or high pH ($OH^-$), mobile ions are introduced, and the presence of these ions produces an increase in the osmotic pressure which drives an increase in the solution uptake. In the presence of NaOH, the formation of $-SO_3^-Na^+$ can produce an increase in osmotic pressure. In the presence of HCl, the mobile $H^+$ ions can produce an increase in osmotic pressure. On the other hand, the H-bonding between $-SO_3H$ groups at low pH could act to suppress hydrogel swelling, producing lower uptakes in acidic solutions than in basic solutions.

The unusual behavior of the Z-HG-PHs makes these unique compositions promising materials for absorption applications. Specifically, the relatively high absorption under acidic or basic conditions is of interest for applications involving the absorption of highly concentrated acids or bases. As a proof-of-concept, the Z-X-Y were used to absorb a 6M HCl solution.

Relatively high uptakes were attained in 5 min (see, FIG. 6A below), and unusually, the uptakes did not decrease significantly during two weeks of immersion. This two-week stability reflects the relatively high chemical stabilities of the Z-X-Y HIPE-templated zwitterionic hydrogels. In contrast, the uptakes in two reference HG-PHs based on acrylamide (AAm), sodium acrylate (NaA), and MBAAm, underwent significant reductions with time, reflecting their degradation. The rapid absorption and high chemical stability of the Z-HG-PHs demonstrate that they are excellent candidates for the collection and storage of acidic solutions.

Temperature Response:

FIGS. 6A-D present comparative plots showing variation in the uptake of a 6 M HCl solution as a function of time (FIG. 6A), the effect of temperature on the water uptake (FIG. 6B), the relative increase in uptake upon immersing water-swollen zwitterionic hydrogels in a 0.75 M NaCl solution (FIG. 6C) and in water at pH 10 (FIG. 6D).

As can be seen in FIGS. 6A-D, water uptake in the Z-X-Y samples was found to be temperature-responsive, wherein a temperature increase from 5 to 60° C. produced a moderate increase in the solution uptake in Z-80-Y and Z-85-Y samples. The temperature-responsive uptake reflects a competing balance of factors: increasing the temperature enhances the chain mobility and the entropy and also reduces the amount of water bound to the MBAAm amide groups, all of which can contribute to a reduction in the water uptake, while on the other hand, increasing the temperature increases the SBMA ionic group mobility and increases the dissociation constant of water, both of which can contribute to an increase in the osmotic pressure, and thus increase uptake. The increase in the osmotic pressure seems to dominate the various factors, producing the moderate increase in uptake with increasing temperature (FIG. 6B). Even a moderate temperature-responsiveness is surprising in light of the lack of temperature-responsiveness in the corresponding non-HIPE-templated Z-0-Y reference sample. This behavior further demonstrates that HIPE-templating enhances the zwitterionic hydrogel's response/sensitivity to various environmental conditions.

Furthermore, the solution uptake increased when the water-swollen hydrogels were immersed in a 0.75 M NaCl solution. The original water uptake was 15.0, 13.6, and 4.4 g $g^{-1}$ for Z-85-5, Z-80-5, and Z-0-5, respectively, and the increase in the equilibrium uptake following immersion was 140%, 90% and 12%, respectively. These results again demonstrate the magnitude of the response amplification that results from the HIPE-templated structure.

The variations of solution uptake with time (uptake rate) are shown in FIG. 6C. After one hour, Z-80-5 and Z-85-10 were approaching their new equilibrium uptakes while Z-0-5 only reached ~30% of its new equilibrium. Even after 5 hours, Z-0-5 remained far from its new equilibrium. This observation demonstrates that HIPE-templating also accelerates the rate of the response to the environment of the zwitterionic hydrogels. The response rates were similarly accelerated for the immersion of the water-swollen Z-X-5 in water at pH 10 (FIG. 6D) or in water at pH 2 (FIG. 5C). It is the micrometer-scale, highly interconnected, highly porous structures which facilitate the capillary action and rapid mass transfer that produce the accelerated response.

CONCLUSIVE REMARKS

Highly interconnected, highly porous Z-HG-PHs with micrometer-scale porosities were successfully synthesized through HIPE templating. The anti-electrolyte behavior produced an increase in the NaCl solution uptake with increasing NaCl concentration. Both the water uptakes and the anti-electrolyte effect increased with increasing porosity and with decreasing crosslinking. Surprisingly, the uptake of urine was up to twice the uptake of water. The Z-X-Y exhibited dual pH-responsive uptakes, decreasing with increasing pH from 2 to 7 and increasing with increasing pH from 7 to 10. The water uptakes of the Z-X-Y increased with increasing temperature (from 5 to 60° C.), in spite of the lack of obvious changes in the corresponding Z-0-Y.

The HIPE-templated structure amplifies the anti-polyelectrolyte effect, the magnitude of the uptake, the sensitivity to changes in the environment, and the response rate to changes in the environment. These enhancements in the behavior of the hydrogels make the highly chemically stable HIPE-templated zwitterionic hydrogels excellent candidates for the collection and storage of aqueous solutions, especially for solutions with relatively high concentrations of electrolytes or acids.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition-of-matter comprising a polymer, the composition-of-matter is having a microstructure of a polymerized external phase of a high internal phase emulsion (HIPE), wherein said polymer comprises a plurality of residues of monomers, at least a portion of which are residues of monomers having a zwitterionic pendant group.

2. The composition-of-matter of claim 1, wherein said polymer is a crosslinked polymer.

3. The composition-of-matter of claim 2, wherein a cross-linking level of said crosslinked polymer ranges from 0.01 to 100 mol percent.

4. The composition-of-matter of claim 1, wherein said plurality of residues of monomers consisting of said residues of monomers having said zwitterionic pendant group.

5. The composition-of-matter of claim 1, characterized by a dry density that ranges from 0.03 g/cm$^3$ to 0.6 g/cm$^3$.

6. A hydrogel comprising the composition-of-matter of claim 1, and an aqueous medium absorbed therein.

7. An article of manufacturing comprising the composition-of-matter of claim 1.

8. A process of preparing the composition-of-matter of claim 1, the process comprising subjecting a high internal phase emulsion (HIPE), having an internal organic phase and a polymerizable external aqueous phase, to polymerization of said polymerizable external aqueous phase, wherein said internal organic phase comprises a water-immiscible solvent, and said polymerizable external aqueous phase comprises a plurality of monomers and at least one cross-linking agent, at least a portion of said monomers is having a zwitterionic pendant group.

9. The process of claim 8, wherein said plurality of monomers is consisting of said monomers having a zwitterionic pendant group.

10. The process of claim 8, wherein said portion of said monomers ranges from 1% to 99% of said plurality of monomers.

11. The process of claim 8, wherein said HIPE comprises a HIPE-stabilizing agent.

12. The process of claim 8, further comprising, prior to said subjecting, forming said HIPE by mixing said internal organic phase and said polymerizable external aqueous phase.

13. The process of claim 12, further comprising, subsequent to said forming said HIPE, adding a polymerization initiator to said HIPE.

14. The process of claim 8, further comprising, subsequent to said subjecting, substantially removing said internal organic phase from the composition-of-matter.

15. The process of claim 14, wherein said removing comprises exchanging said water-immiscible organic solvent or melt with a water-miscible organic solvent.

16. The process of claim 15, wherein said exchanging is effected by immersion at a temperature lower than 0° C.

17. The process of claim 15, further comprising, subsequent to said exchanging, subjecting the composition-of-matter to extraction in said water-miscible organic solvent, and drying the composition-of-matter from said water-miscible organic solvent.

* * * * *